US010289898B2

(12) United States Patent
el Kaliouby et al.

(10) Patent No.: US 10,289,898 B2
(45) Date of Patent: *May 14, 2019

(54) VIDEO RECOMMENDATION VIA AFFECT

(71) Applicant: Affectiva, Inc., Waltham, MA (US)

(72) Inventors: Rana el Kaliouby, Milton, MA (US); Abdelrahman Mahmoud, Somerville, MA (US); Panu James Turcot, San Francisco, CA (US)

(73) Assignee: Affectiva, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/357,585

(22) Filed: Nov. 21, 2016

(65) Prior Publication Data

US 2017/0068847 A1 Mar. 9, 2017

Related U.S. Application Data

(63) Continuation-in-part of application No. 15/262,197, filed on Sep. 12, 2016, now abandoned, and a
(Continued)

(51) Int. Cl.
*G06K 9/00* (2006.01)
*A61B 5/16* (2006.01)
(Continued)

(52) U.S. Cl.
CPC .......... *G06K 9/00302* (2013.01); *A61B 5/165* (2013.01); *G06K 9/00711* (2013.01);
(Continued)

(58) Field of Classification Search
CPC ............... A61B 5/165; G06K 9/00302; G06K 9/00711; G06K 2009/00328;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Nathan J Flynn
*Assistant Examiner* — Cynthia M Fogg
(74) *Attorney, Agent, or Firm* — Adams Intellex, PLC

(57) ABSTRACT

Analysis of mental state data is provided to enable video recommendations via affect. Analysis and recommendation is made for socially shared live-stream video. Video response is evaluated based on viewing and sampling various videos. Data is captured for viewers of a video, where the data includes facial information and/or physiological data. Facial and physiological information is gathered for a group of viewers. In some embodiments, demographic information is collected and used as a criterion for visualization of affect responses to videos. In some embodiments, data captured from an individual viewer or group of viewers is used to rank videos.

36 Claims, 16 Drawing Sheets

Related U.S. Application Data continuation-in-part of application No. 14/821,896, filed on Aug. 10, 2015, now Pat. No. 9,503,786, said application No. 15/262,197 is a continuation-in-part of application No. 14/796,419, filed on Jul. 10, 2015, now abandoned, which is a continuation-in-part of application No. 14/460,915, filed on Aug. 15, 2014, said application No. 14/821,896 is a continuation-in-part of application No. 13/406,068, filed on Feb. 27, 2012, now Pat. No. 9,106,958, said application No. 14/796,419 is a continuation-in-part of application No. 13/153,745, filed on Jun. 6, 2011, now abandoned, said application No. 14/460,915 is a continuation-in-part of application No. 13/153,745, filed on Jun. 6, 2011, now abandoned.

(60) Provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/581,913, filed on Dec. 30, 2011, provisional application No. 61/580,880, filed on Dec. 28, 2011, provisional application No. 61/568,130, filed on Dec. 7, 2011, provisional application No. 61/549,560, filed on Oct. 20, 2011, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.
*G06Q 30/06* (2012.01)
*H04N 21/25* (2011.01)
*H04N 21/4223* (2011.01)
*H04N 21/442* (2011.01)
*H04N 21/466* (2011.01)

(52) U.S. Cl.
CPC ....... *G06Q 30/0631* (2013.01); *H04N 21/251* (2013.01); *H04N 21/252* (2013.01); *H04N 21/4223* (2013.01); *H04N 21/44218* (2013.01); *H04N 21/4667* (2013.01); *H04N 21/4668* (2013.01); *G06K 2009/00328* (2013.01)

(58) Field of Classification Search
CPC ............. G06K 9/0053; H04N 21/4223; H04N 21/44218; H04N 21/4668; H04N 21/251; H04N 21/252; H04N 21/4667; H04N 21/42201; H04N 21/44213; H04N 21/4826; G06Q 30/0201
USPC ........................................................ 725/9–12
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 * | 3/2006 | Hendricks ......... G06F 17/30017 348/E5.002 |

(56) References Cited

U.S. PATENT DOCUMENTS

| | | |
|---|---|---|
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 7,949,561 B2 | 5/2011 | Briggs |
| 8,010,458 B2 | 8/2011 | Galbreath et al. |
| 8,046,798 B1 * | 10/2011 | Schlack ............ G06Q 30/02 |
| | | 725/10 |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 * | 5/2003 | Dimitrova ............ H04N 7/163 |
| | | 725/10 |
| 2003/0191682 A1 | 10/2003 | Shepard et al. |
| 2003/0191816 A1 | 10/2003 | Landress et al. |
| 2004/0098744 A1 * | 5/2004 | Gutta ............ G06F 17/30828 |
| | | 725/46 |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 * | 12/2005 | Tavares ............ G06K 9/00221 |
| | | 725/10 |
| 2006/0019224 A1 | 1/2006 | Behar et al. |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0214903 A1 | 9/2008 | Orbach |
| 2008/0221472 A1 | 9/2008 | Lee et al. |
| 2008/0222671 A1 | 9/2008 | Lee et al. |
| 2008/0287821 A1 | 11/2008 | Jung et al. |
| 2008/0292151 A1 | 11/2008 | Kurtz et al. |
| 2008/0295126 A1 | 11/2008 | Lee et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0144071 A1 * | 6/2009 | Saito ............ G06Q 30/02 |
| | | 705/346 |
| 2009/0150919 A1 * | 6/2009 | Lee ............ H04N 7/17309 |
| | | 725/10 |
| 2009/0177528 A1 | 7/2009 | Wu et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0281497 A1 | 11/2010 | Miyazaki |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2011/0301433 A1 | 12/2011 | Sadowsky et al. |
| 2012/0072939 A1 * | 3/2012 | Crenshaw ............ H04H 60/33 |
| | | 725/12 |
| 2012/0124456 A1 * | 5/2012 | Perez ............ G06Q 30/02 |
| | | 715/200 |
| 2012/0324491 A1 * | 12/2012 | Bathiche ............ H04H 60/33 |
| | | 725/10 |
| 2013/0023337 A1 | 1/2013 | Bowers et al. |
| 2013/0116587 A1 | 5/2013 | Sornmo et al. |
| 2013/0197409 A1 | 8/2013 | Baxter et al. |
| 2013/0242064 A1 * | 9/2013 | Herdy ............ H04N 5/4403 |
| | | 348/51 |
| 2015/0135225 A1 * | 5/2015 | Bayer ............ H04N 21/4826 |
| | | 725/46 |

FOREIGN PATENT DOCUMENTS

| | | |
|---|---|---|
| KR | 10-2008-0016303 A | 2/2008 |
| KR | 10-2010-0021702 A | 2/2010 |
| KR | 1020100048688 A | 5/2010 |
| KR | 10-2011-0047718 A | 5/2011 |
| WO | WO 02/43391 A1 | 5/2002 |
| WO | WO 2011/045422 A1 | 4/2011 |

OTHER PUBLICATIONS

International Search Report dated Nov. 14, 2011 for PCT/US2011/039282.

International Search Report dated Apr. 16, 2012 for PCT/US2011/054125.

International Search Report dated May 24, 2012 for PCT/US2011/060900.

(56) References Cited

OTHER PUBLICATIONS

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

International Search Report dated May 15, 2013 for PCT/US2012/068496.

The State Intellectual Property Office of China Office Action dated Jul. 23, 2014 for Application No. 201180053869.7.

Albiol, Alberto, et al. "Face recognition using HOG-EBGM." Pattern Recognition Letters 29.10 (2008): 1537-1543.

* cited by examiner

VIDEO RECOMMENDATION VIA AFFECT

RELATED APPLICATIONS

This application is a continuation-in-part of U.S. patent application "Video Recommendation Using Affect" Ser. No. 14/821,896, filed Aug. 10, 2015, which is a continuation-in-part of U.S. patent application "Video Recommendation Based on Affect" Ser. No. 13/406,068, filed Feb. 27, 2012, which claims the benefit of U.S. provisional patent applications "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertising" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011.

This application is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016. The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015. The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014. The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. Each of the foregoing applications is hereby incorporated by reference in its entirety.

FIELD OF INVENTION

This application relates generally to analysis of mental states and more particularly to making video recommendations based on affect.

BACKGROUND

People spend a tremendous amount of time viewing and interacting with videos. The videos are viewed in numerous contexts including educational settings, entertainment, to obtain daily news, and many others. A video may be a movie, a television show, a web series, a webisode, a video, a music video, or a video clip and may be viewed as a stand-alone element on an electronic display, or as part of a webpage. Evaluation of these videos and individual responses to them is exceedingly important in gauging the effectiveness of platforms such as education, commerce, and entertainment, among others, which is why rating systems are often employed to give people the opportunity to respond to video content. To self-rate videos, people can use the often-tedious means of entering a specific number of stars corresponding to a level of like or dislike, or they may answer a list of questions. It is even more tedious and difficult to evaluate portions of videos, where evaluation of a brief period of time from a video may be useful. Recommendations based on such a star rating are imprecise, subjective, and often unreliable.

SUMMARY

A computer implemented method is disclosed for affect-based recommendations comprising: playing a first media presentation to an individual; capturing mental state data for the individual while the first media presentation is played; and recommending a second media presentation to the individual based on the mental state data for the individual which was captured. The method can further comprise comparing the mental state data that was captured for the individual against a plurality of mental state event temporal signatures. The method can further comprise analyzing the mental state data to produce mental state information. The method can further comprise correlating the mental state data which was captured for the individual to mental state data collected from other people who experienced the first media presentation. The recommending the second media presentation to the individual can be further based on the correlating between the individual and the other people. The recommending the second media presentation to the individual can be further based on the comparing. The first media presentation can include one of a group consisting of a movie, a television show, a web series, a webisode, a video, a video clip, an electronic game, an e-book, and an e-magazine. The second media presentation can include one of a group consisting of a movie, a television show, a web series, a webisode, a video, a video clip, an electronic game, an e-book, and an e-magazine. The first media presentation can be played on a web-enabled interface. The first media presentation can include one of a YouTube™, a Vimeo™ video, and a Netflix™ video. The second media presentation can include one of a YouTube™, a Vimeo™ video, and a Netflix™ video. The method can further comprise ranking the first media presentation relative to another media presentation based on the mental state data which was captured. The ranking can be for the individual and based on the mental state data from the individual. The ranking can be based on anticipated preferences for the individual.

The mental state data can be captured from multiple people and can further comprise aggregating the mental state data from the multiple people. The method can further comprise ranking the first media presentation relative to another media presentation based on the mental state data which was aggregated from the multiple people. The mental state data can include one of a group consisting of physiological data, facial data, and actigraphy data. The facial data can include information on one or more of a group consisting of facial expressions, action units, head gestures, smiles, brow furrows, squints, lowered eyebrows, raised eyebrows, smirks, and attention. The physiological data can include one or more of electrodermal activity, heart rate, heart rate variability, skin temperature, and respiration. The method can further comprise inferring of mental states based on the mental state data which was collected. The mental states can include one of a group consisting of frustration, confusion, disappointment, hesitation, cognitive overload, focusing, being engaged, attending, boredom, exploration, confidence, trust, delight, valence, skepticism, and satisfaction. The method can further comprise matching a first event signature, from the plurality of mental state event temporal signatures, against the mental state data that was captured. The playing of the first media presentation can be done on a mobile device and can further comprise the recording of facial images with the mobile device as part of the capturing of the mental state data.

In embodiments, a computer program product is stored on a non-transitory computer-readable medium for affect based recommendations, the computer program product comprising code which causes one or more processors to perform operations of: playing a first media presentation to an individual; capturing mental state data for the individual, wherein the mental state data includes video facial data from the individual during the first media presentation playing; comparing the mental state data that was captured for the individual against a plurality of mental state event temporal signatures; ranking the first media presentation relative to another media presentation based on the mental state data which was captured for the individual, wherein the ranking is for the individual; and recommending a second media presentation to the individual based on the mental state data which was captured for the individual, wherein the recommending the second media presentation to the individual is further based on the compared mental state data. In some embodiments, a computer system for affect-based recommendations can comprise: a memory for storing instructions; one or more processors attached to the memory wherein the one or more processors are configured to: play a first media presentation to an individual; capture mental state data for the individual, wherein the mental state data includes video facial data from the individual during the first media presentation playing; compare the mental state data that was captured for the individual against a plurality of mental state event temporal signatures; rank the first media presentation relative to another media presentation based on the mental state data which was captured for the individual, wherein the ranking is for the individual; and recommend a second media presentation to the individual based on the mental state data which was captured for the individual, wherein the recommending the second media presentation to the individual is further based on the compared mental state data.

In some embodiments, a computer implemented method for affect based ranking can comprise: displaying a plurality of media presentations to a group of people; capturing mental state data from the group of people while the plurality of media presentations is displayed; correlating the mental state data captured from the group of people who viewed the plurality of media presentations; and ranking the media presentations relative to one another based on the mental state data. The method can further comprise tagging the plurality of media presentations with mental state information based on the mental state data which was captured.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Presently disclosed are various methods and systems for analyzing people's mental states as the people view videos. The ability to properly evaluate people's individual and collective response to videos enables the accurate recommendation of other videos. The videos can be for any purpose and can be of any type including entertaining, educational, or generally informative. The evaluation of mental states in response to videos provides unmatched insight into people's true reactions to the videos. As used in this disclosure, a mental state can be an emotional state or a cognitive state. Where happiness or sadness can be considered examples of emotional states, concentration or confusion can be identified as cognitive states. Observing, capturing, and analyzing these mental states can yield significant information about people's reactions to a video. Some terms commonly used in the evaluation of mental states are arousal and valence. Arousal is an indication on the amount of activation or excitement of a person. Valence is an indication on whether a person is positively or negatively disposed. Valence can range from being very positive, such as when someone is happy, to being very negative, such as when someone is angry. A third common term, affect, can include analysis of arousal and valence and can also include facial analysis for expressions, such as smiles or brow furrowing. Affect is an observable expression of emotion. A person's affect is the expression of emotion or feelings, generally displayed to others through observable means such as facial expressions, hand gestures, voice quality, and other emotional cues. Affect analysis might be as simple as tracking when someone smiles or when someone frowns while viewing a video, or it might be much more complex. Recommendations for other videos, in some embodiments, are made based on tracking when someone smiles while watching one or more videos and recommending videos with similarities to those videos which made the individual smile.

Figure 1:
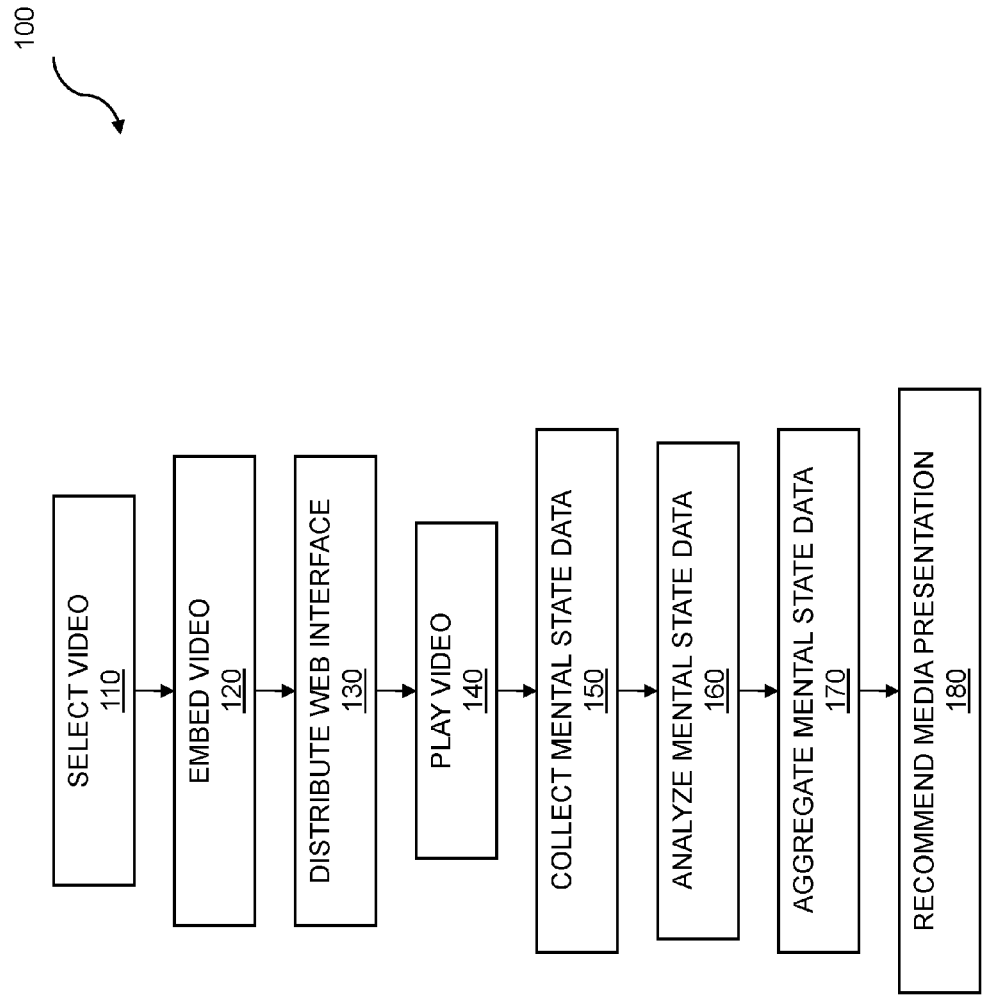
FIG. 1 is a flow diagram for displaying a video.

FIG. 1 is a flow diagram for displaying a video. A flow 100 is shown for a computer-implemented method for rendering video. The flow 100 begins with selecting a video 110. The video can be selected by a system which is automating the collection of affect on numerous videos. In embodiments, the video is selected by a person who wants affect collected on the video. The video can include one of a YouTube™ and a Vimeo™ video. The flow 100 continues with embedding the video 120 within a web-enabled interface, wherein the web-enabled interface activates collecting of mental state data. The web-enabled interface can include a web page, a web application, or the like. The embedding 120 can include inserting a link for the video as a URL on a web page that activates affect collection. The embedding 120 can include providing a link where a user can insert their own video. The affect can be collected by evaluating facial expressions. The evaluating facial expressions can include evaluating smiles or brow furrows. The affect can include evaluation of one of a group consisting of attention, engagement, interest, liking, and disliking. The affect can be collected by evaluating physiology.

The flow 100 continues with distributing the web-enabled interface 130. The distributing of the web-enabled interface can include sending a URL. The sending of the URL can be accomplished using one of a group consisting of an email, a text message, a Facebook™ posting, a Twitter™ message, a Google+™ posting, a LinkedIn™ posting, a social network update, and a blog entry. In some embodiments, the sending is accomplished by pressing or selecting a button on a web page associated with a video. Selecting the button can distribute the video. In some embodiments, selecting the button also distributes mental state data or analysis of mental state data along with the video. The flow 100 further comprises playing the video 140, perhaps in the web-enabled interface, and collecting the mental state data 150 while the video is being played. The mental state data can be collected for a group of people who view the video.

The mental state data collected can include one of a group consisting of physiological data, facial data, and actigraphy data. The physiological data can include one or more of electrodermal activity, heart rate, heart rate variability, skin temperature, and respiration. The facial data can include information on one or more of a group consisting of facial expressions, action units, head gestures, smiles, brow furrows, squints, lowered eyebrows, attention, and the like. The mental states that can be inferred can include one of a group consisting of frustration, confusion, disappointment, hesitation, cognitive overload, focusing, being engaged, attending, boredom, exploration, confidence, trust, delight, frustration, valence, skepticism, and so on. The mental state data can be collected for an individual. Likewise, the mental state data can be captured from multiple people.

The flow 100 continues with analyzing mental state data 160. The mental state data can be analyzed 160 to produce mental state information. Mental states for a viewer or a plurality of viewers can be inferred based on the mental state data which was collected. The flow 100 continues with aggregating mental state data 170. Mental state data can be collected from multiple people who view a video, and the mental state data from the multiple people can be aggregated. In doing so, the mental state data can be aggregated across a group of people. Results from the aggregating 170 can be presented as part of the displaying of a graphical representation.

The flow 100 further comprises recommending a media presentation 180. The aggregating of the mental state data 170 can be used as part of the input to result in recommending a media presentation 180 to an individual based on the mental state data which was aggregated. The media presentation can be one of a group consisting of a movie, a television show, a web series, a webisode, a video, a video clip, an electronic game, an advertisement, an e-book, and an e-magazine. The flow 100 can further comprise recommending a media presentation to a second person based on the mental state data collected from a first person. Various steps in the flow 100 may be changed in order, repeated, omitted, or the like without departing from the disclosed inventive concepts. Various embodiments of the flow 100 may be included in a computer program product embodied in a non-transitory computer readable medium that includes code executable by one or more processors. The flow 100 can include tagging the plurality of media presentations with mental state information based on the mental state data which was captured.

Figure 2:
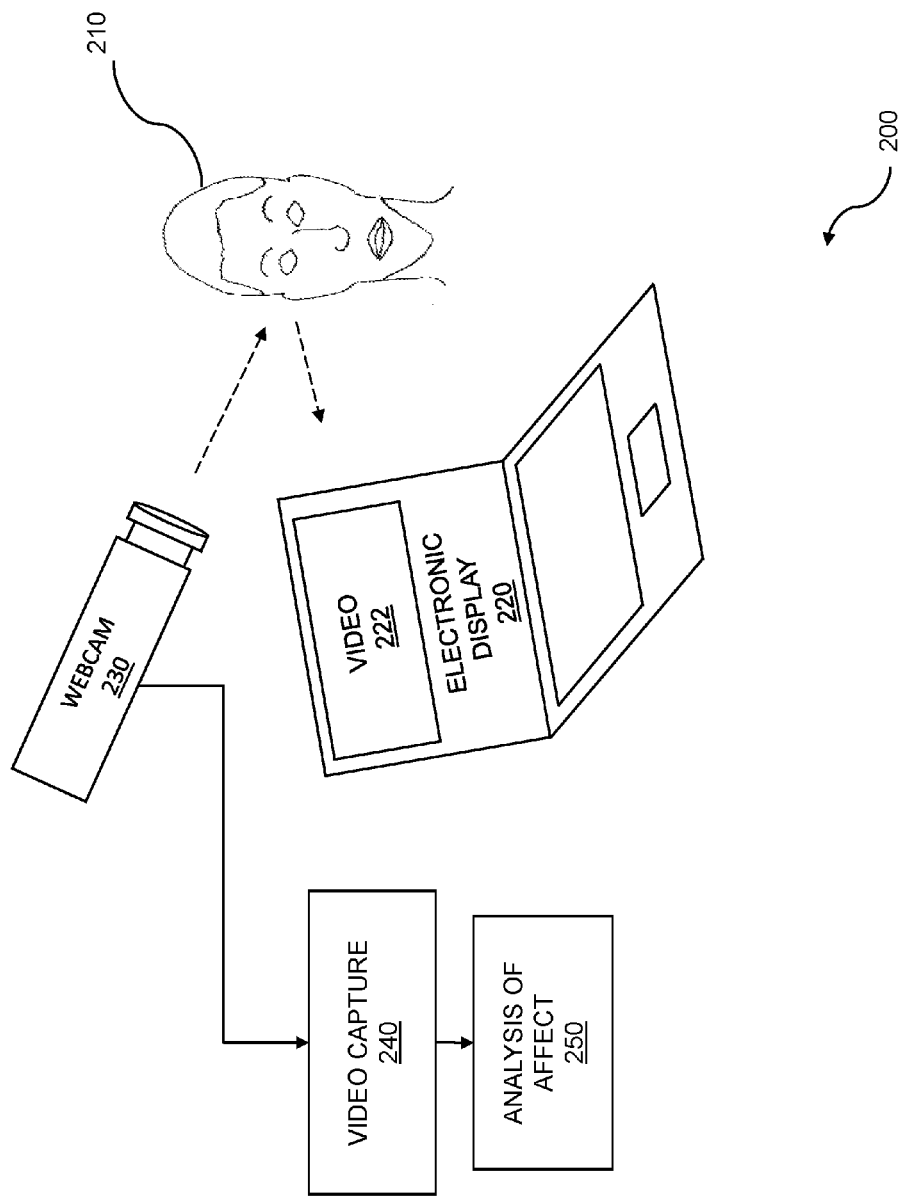
FIG. 2 is a system for capturing facial response to a video.

FIG. 2 is a system for capturing facial response to a video. A system 200 includes an electronic display 220 and a webcam 230. The system 200 captures facial response to a video 222 shown on the electronic display 220. The facial data can include video and collection of information relating to mental states. The facial data can include information on one or more of a group consisting of facial expressions, action units, head gestures, smiles, brow furrows, squints, lowered eyebrows, raised eyebrows, smirks, and attention. In some embodiments, a webcam 230 captures video of the person 210. Images of the person 210 can also be captured by a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that can allow image data captured to be used by an electronic system. The capture of the facial response of the person 210 to the video 222 shown on the display 220 can include collection of mental state data. The capture of the facial response of the person 210 to the video 222 shown on the display 220 can include capture of physiological data. The physiological data can include one or more of heart rate, heart rate variability, skin temperature, respiration, and the like.

The electronic display 220 can show a video. The video 222 can be shown on any electronic display, including but not limited to, a computer display, a laptop screen, a net-book screen, a tablet computer screen, a cell phone display, a mobile device display, a remote with a display, a television, a projector, or the like. The electronic display 220 can include connections to a keyboard, mouse, joystick, touchpad, wand, motion sensor, and other input means. The video 222 can be displayed within a webpage, a website, a web-enabled application, or the like. The images of the person 210 can be captured by a video capture unit 240. In some embodiments, video of the person 210 is captured, while in others, a series of still images are captured.

Analysis of action units, gestures, mental states, and physiological data can be accomplished using the captured images of the person 210. The action units can be used to identify smiles, frowns, and other facial indicators of mental states. The gestures, including head gestures, can indicate interest or curiosity. For example, a head gesture of moving toward the video 222 can indicate increased interest or a desire for clarification. Based on the captured images, analysis of physiology, or affect, can be performed. Analysis of affect 250 can be performed based on the information and images which are captured. The analysis can include facial analysis and analysis of head gestures. The analysis can include evaluating physiology and evaluating one of a group consisting of heart rate, heart rate variability, respiration, perspiration, temperature, and other bodily evaluations.

Figure 3:
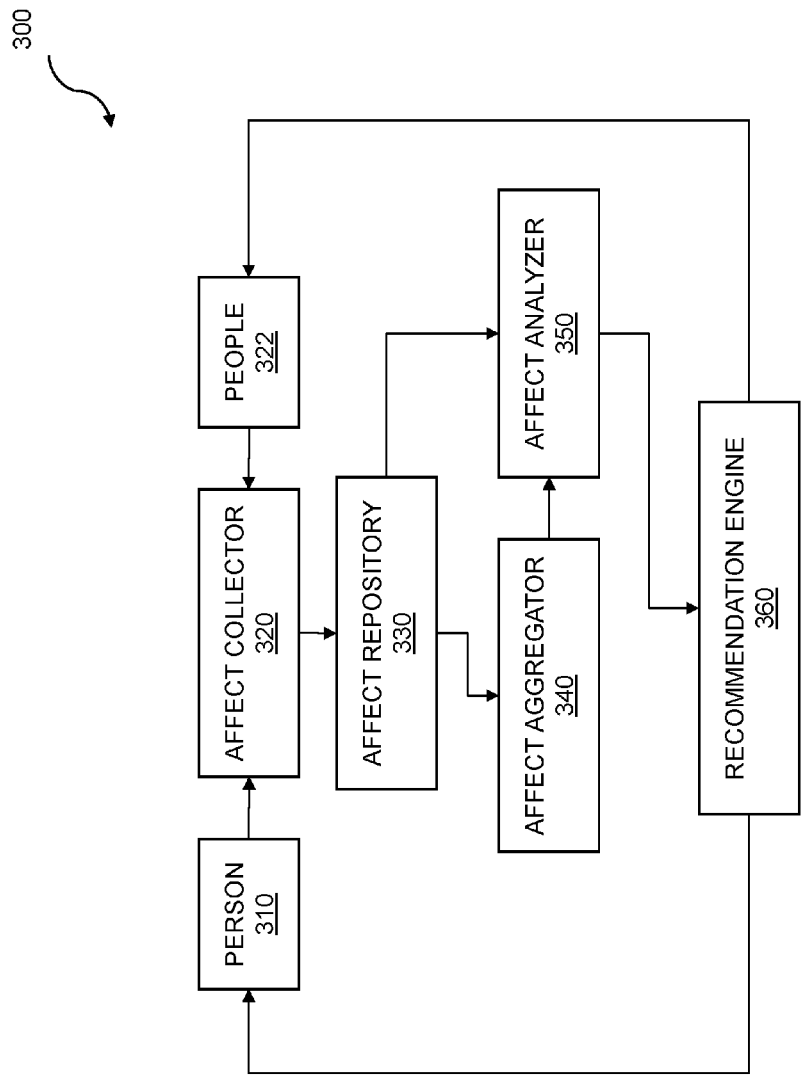
FIG. 3 is a diagram of a recommendation system.

FIG. 3 is a diagram of a recommendation system. In the flow 300, a person 310 can view a video. While the person 310 is viewing a video, an affect collector 320 can gather affect data on the person 310. The affect collector 320 can be a webcam or another camera device. The affect collector 320 can be a biosensor attached to the person 310 in one or more locations. The affect data collected from the person 310 by the affect collector 320 can be stored in an affect repository 330. The affect repository 330 can be on a local computer or on a remote server, or it can be distributed as part of a cloud computing system.

An affect analyzer 350 can analyze the affect data collected from the person 310. The affect analyzer 350 can recognize mental states including information on concentration, liking, disliking, etc. The affect analyzer 350 can recognize smiles or frowns. Based on the analysis done by the affect analyzer 350, a recommendation engine 360 can recommend a video or another media presentation to the person 310. The recommending of a media presentation to an individual can be based on the mental state data which was aggregated. The aggregated data can be for multiple videos by an individual, or it can be for a plurality of people. The recommendation can be based on common factors with one or more videos which the person 310 watched. For example, if the person 310 smiled for each of the videos that he or she watched that featured a specific actress as the main character, then the recommendation engine 360 can recommend another video with the same actress to the person 310. In another example, if a series of sports videos is liked by the person 310, then another sports video can be recommended.

Other people 322 can view the same video as the person 310. In some embodiments, multiple videos are viewed by the person 310 and the other people 322. In embodiments, different subsets of the multiple videos are viewed by each person. The affect collector 320 can capture affect data for each of the people 322. The affect collector 320 can be a single unit such as a kiosk in a mall or a device which collects affect for multiple people viewing a video in such a location as a conference room or a movie theater. Alternatively, the affect collector 320 can be separate devices, if, for instance, each person has their own computer, laptop, cell phone, mobile device, or the like. The affect repository 330 can retain affect data from the people on whom affect data is collected.

An affect aggregator 340 can take affect data from the affect repository 330 and correlate affect data from the person 310 with the other people 322. The affect aggregator 340 can recognize trends for the person 310 who has watched multiple videos such as movies. The affect aggregator 340 can determine correlation vectors for the person 310 and the people 322 or a subset thereof. A correlation can be made using weighted Euclidean or Mahalanobis distance evaluation between two vectors, where a vector includes an individual's affect data. There are many ways to compute distances or similarity/dissimilarity measures. Collaborative filtering or the like can be used to aid in matching affect data between or among people. In some embodiments, a comparison is made based on the same content viewed by the person 310 and by individuals from the other people 322. When one vector is at a sufficiently small distance from another person's vector, then the affect aggregator 340 will look for other content that has been smiled at or liked. This other content can be recommended by the recommendation engine 360 to the person 310 because there are assumed similarities based on the affect data which was collected.

In some embodiments, the affect aggregator 340 and the affect analyzer 350 are used to review affect data stored in the affect repository 330 to compare affect data collected on a new video with an historical database of affect data for videos. The new video can be evaluated to determine how the video ranks against other videos. For example, the new video could be compared with a "top 100" list of videos to determine the relative number of smiles that the new video has in comparison to the "top 100" list of videos for which people smiled. In embodiments, a group of people view a new video and have affect data collected. The affect data collected for the people can be aggregated together. The aggregated affect data for the new video can then be compared to the aggregated affect data for other videos. This type of comparison could be used by developers of videos to rank and evaluate a new video which has been produced.

Likewise, a buyer of advertising spots, for example, could evaluate a new video based on aggregated affect data collected from a group of people. An emotion profile for the video could be generated and then compared with a "best of breed" set of videos by network studios, advertisers, or others with similar commercial interest.

In some cases, there may be good correlation for one type of video but not for another. For instance, a good correlation can be made for drama videos but a poor one for comedy videos. Based on that information, a recommendation can be made for another drama video. Collaborative filtering can be performed to identify good possibilities for correlation, and therefore areas where videos can be recommended.

The recommendation engine 360 can make recommendations to the person 310 on whom affect was collected. The recommendation engine 360 can make the recommendations based on the correlation between the person 310 and the other people 322. Likewise, the recommendation engine 360 can make recommendations to one or more of the people 322 based on a video that was viewed by the person 310.

Figure 4:
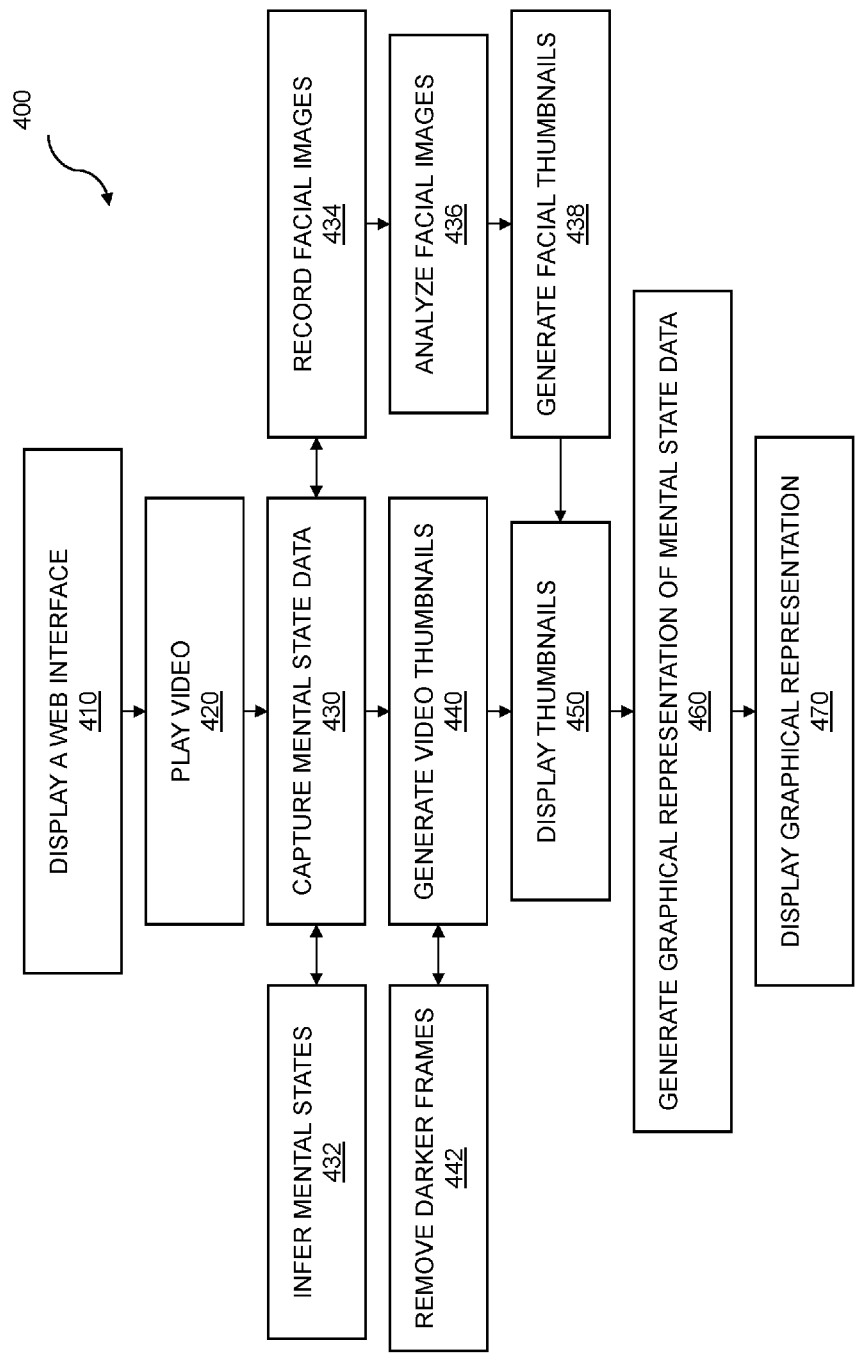
FIG. 4 is a flow diagram for displaying affect.

FIG. 4 is a flow diagram for displaying affect. The flow 400 describes a computer-implemented method for displaying affect. The flow 400 begins with displaying a first web-enabled interface 410. The first web-enabled interface can include a web page. The flow 400 continues with playing a video 420 on the first web-enabled interface. The video can include a YouTube™ or a Vimeo™ video. The video can be one of a group consisting of a movie, a television show, a web series, a webisode, a video, a video clip, or the video can be media such as an electronic game, an advertisement, an e-book, an e-magazine, or a movie trailer. The flow 400 continues with capturing mental state data 430 while the video is played. The flow can further comprise inferring of mental states 432 based on the mental state data which was collected. The mental states can include one of a group consisting of frustration, confusion, disappointment, hesitation, cognitive overload, focusing, being engaged, attending, boredom, exploration, confidence, trust, delight, valence, skepticism, and satisfaction.

The capturing mental state data can further comprise recording facial images 434. The flow 400 further comprises analyzing the facial images for a facial expression 436. The facial data can include information on one or more of a group consisting of facial expressions, action units, head gestures, smiles, brow furrows, squints, lowered eyebrows, raised eyebrows, smirks, attention, and the like. The facial expressions can be used to generate facial thumbnails 438. In some embodiments, representative low-resolution images are included in the thumbnails rather than images obtained directly from a webcam or another imaging apparatus.

The flow 400 continues with generating a set of thumbnails 440 for the video which was played, where the thumbnails comprise scenes from the video and the set of thumbnails are generated automatically. The flow 400 further comprises analyzing the set of thumbnails and removing a frame 442 from the set of thumbnails based on a dark threshold. Another frame can be used in place of the frame that was removed. The flow 400 continues with displaying the set of thumbnails 450 on a second web-enabled interface. The second web-enabled interface can include a web page. In embodiments, the thumbnails are for the video which was played.

In embodiments, an individual thumbnail is one "scene" from the video and is a static image of a specified size. Various items can be useful in the generation of thumbnails and are briefly discussed here. A composite of thumbnails or zoetrope is a horizontal array of images. A dark threshold is used to analyze a mean value of the color of an image to determine whether it is "dark." A starting offset is a number of seconds into the video in which to begin the thumbnail generation process. A number of seconds between frames can be automatically generated or specified manually and refers to the number of seconds between the individual thumbnail images. A zoetrope width is the width of the final image and can be slightly different from the width of an individual thumbnail multiplied by the number of thumbnails. A size string can be of the form, "width times height", and examples of potential size strings include dimensions of 24×24, 32×32, 40×32, etc. The size string determines the dimensions of the individual thumbnail. The individual thumbnails can be examined to determine if the image is "too dark." Some movie trailers frequently fade to black, and black or very dark frames often make for poor thumbnails. A recursive look forward and backward to find a better frame is possible. If a frame is too dark, then the recursive algorithm looks behind and forward by small amounts to see if it can find a better frame that can be found within certain recursion limits. Once a good image is found or a recursion limit is reached, the video is advanced by the appropriate number of seconds between frames to identify the next thumbnail image.

In some embodiments, the flow 400 further comprises generating a set of thumbnails for the facial images which were recorded 438 and displaying the set of thumbnails 450 for the facial images on the second web-enabled interface. One thumbnail from the set of thumbnails can be selected based on a facial expression. The one thumbnail can show an animated facial expression, an unusual facial expression, or a typical facial expression.

The flow 400 continues with generating a graphical representation of the mental state data 460 which was captured. The graphical representation can be a line graph showing an amount of a specific mental state or an amount of a specific facial expression. Likewise, the graphical representation can be a more complex dashboard-type presentation. The flow 400 can continue with displaying the graphical representation 470 on the second web-enabled interface. The graphical representation can include a score representing the mental state data. The score can be for a specific mental state, such as attention, frustration, disappointment, or any other mental state. The score can provide a numerical representation of the mental state.

In some embodiments, the playing of the video is done on a mobile device and the recording of the facial images is done with the mobile device. In embodiments, the mental state data is captured from multiple people and aggregated. Various steps in the flow 400 may be changed in order, repeated, omitted, or the like without departing from the disclosed inventive concepts. Various embodiments of the flow 400 may be included in a computer program product embodied in a non-transitory computer readable medium that includes code executable by one or more processors.

Figure 5:
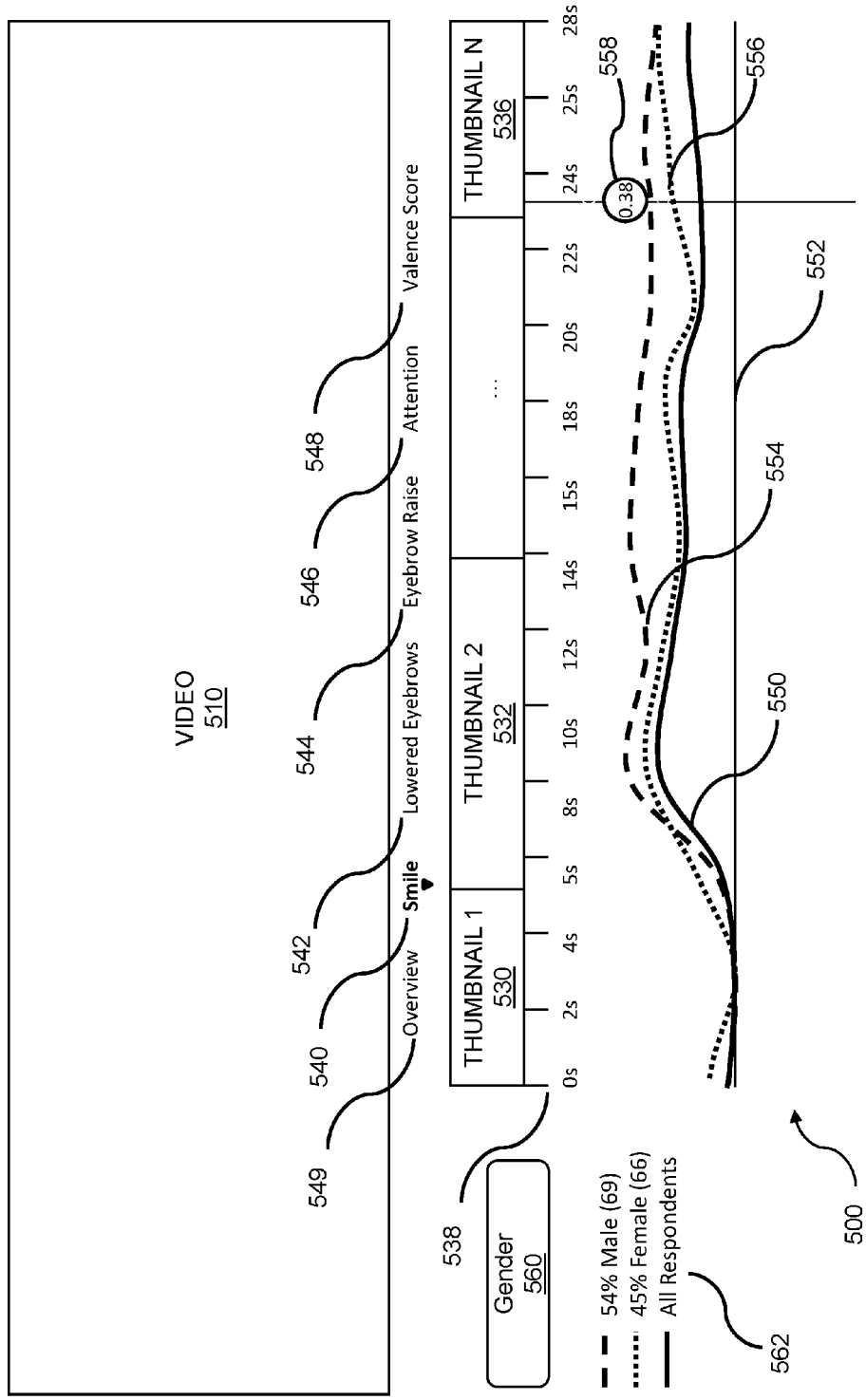
FIG. 5 is a graphical representation of displaying affect.

FIG. 5 is an example graphical representation of displaying affect. The display 500, or dashboard, is a graphical representation of mental state analysis that can be shown for video viewer analysis and can be presented on an electronic display. The display can be a television monitor, projector, computer monitor (including a laptop screen, a tablet screen, a net-book screen, and the like), a cell phone display, a mobile device, or another electronic display. In embodiments, the display is a webpage. The example display 500 is shown which includes a rendering of a video 510 along with associated mental state information. The visualization can further comprise the rendering related to the video 510. A user can select among a plurality of video renderings using various buttons and/or tabs. The user interface allows a plurality of parameters to be displayed as a function of time, synchronized to the video rendering 510. Various embodiments have any number of selections available for the user, and some include other types of renderings instead of video. A set of thumbnail images for the selected rendering are shown in the example, including Thumbnail 1 530 and Thumbnail 2 532 through Thumbnail N 536 which can be displayed below the rendering along with a timeline 538. The thumbnails can show a graphic "storyboard" of the video rendering. This storyboard can assist a user in identifying a particular scene or location within the video rendering. Some embodiments do not include thumbnails or have a single thumbnail associated with the rendering, while various other embodiments have thumbnails of equal length and others have thumbnails of differing lengths. In some embodiments, the start and/or end of the thumbnails is determined based on changes in the captured viewer mental states associated with the rendering, or are based on particular points of interest in the video rendering. Thumbnails of one or more viewers can be shown along the timeline 538. The thumbnails of viewers can include peak expressions, expressions at key points in the video rendering 510, etc.

Some embodiments include the ability for a user to select a particular type of mental state information for display using various buttons or other selection methods. The mental state information can be based on one or more descriptors. The one or more descriptors can include, but are not limited to, one of action unit 4 (AU4), action unit 12 (AU12), and valence. By way of example, the smile mental state information is shown in the display 500 as the user might have previously selected the Smile button 540. Other types of mental state information that can be available for user selection in various embodiments include the Lowered the Eyebrows button 542, the Eyebrow Raise button 544, the Attention button 546, the Valence Score button 548, or other types of mental state information, depending on the embodiment. An Overview button 549 can be available to allow a user to show graphs of the multiple types of mental state information simultaneously. The mental state information can include probability information for one or more descriptors, and the probabilities for the one of the one or more descriptors can vary for portions of the video rendering.

Because the Smile button 540 has been selected in the example shown, a smile graph 550 can be shown against a baseline 552, showing the aggregated smile mental state information of the plurality of individuals from whom mental state data was collected for the video. The male smile graph 554 and the female smile graph 556 can be shown so that the visual representation displays the aggregated mental state information. These graphs are provided by way of example only, as the mental state information can be based on a demographic basis as those viewers who comprise that demographic react to the video. The analysis of the mental state data can be based on a demographic basis. The various demographic based graphs can be indicated using various line types as shown, or they can be indicated using color or another method of differentiation. A slider 558 can allow a user to select a particular time of the timeline and show the value of the chosen mental state for that particular time. The video 510 can be coordinated with the slider 558. The slider 558 is selected and moved with a mouse or another pointing device, in some embodiments. The video 510 can jump to the point in time to which the slider 558 has been moved. The mental states can be used to evaluate the value of the video.

In some embodiments, various types of demographic-based mental state information is selected using the demographic button 560. Such demographics can include gender, age, race, income level, education, or any other type of demographic, including dividing the respondents into those respondents that had higher reactions from those with lower reactions. A graph legend 562 can be displayed indicating the various demographic groups, the line type or color for each group, the percentage of total respondents and/or the absolute number of respondents for each group, and/or other information about the demographic groups. The mental state information can be aggregated according to the demographic type selected. Thus, aggregation of the mental state information is performed on a demographic basis so that mental state information is grouped based on the demographic basis, for some embodiments. The video thus can be evaluated for responses by various demographic groups.

Figure 6:
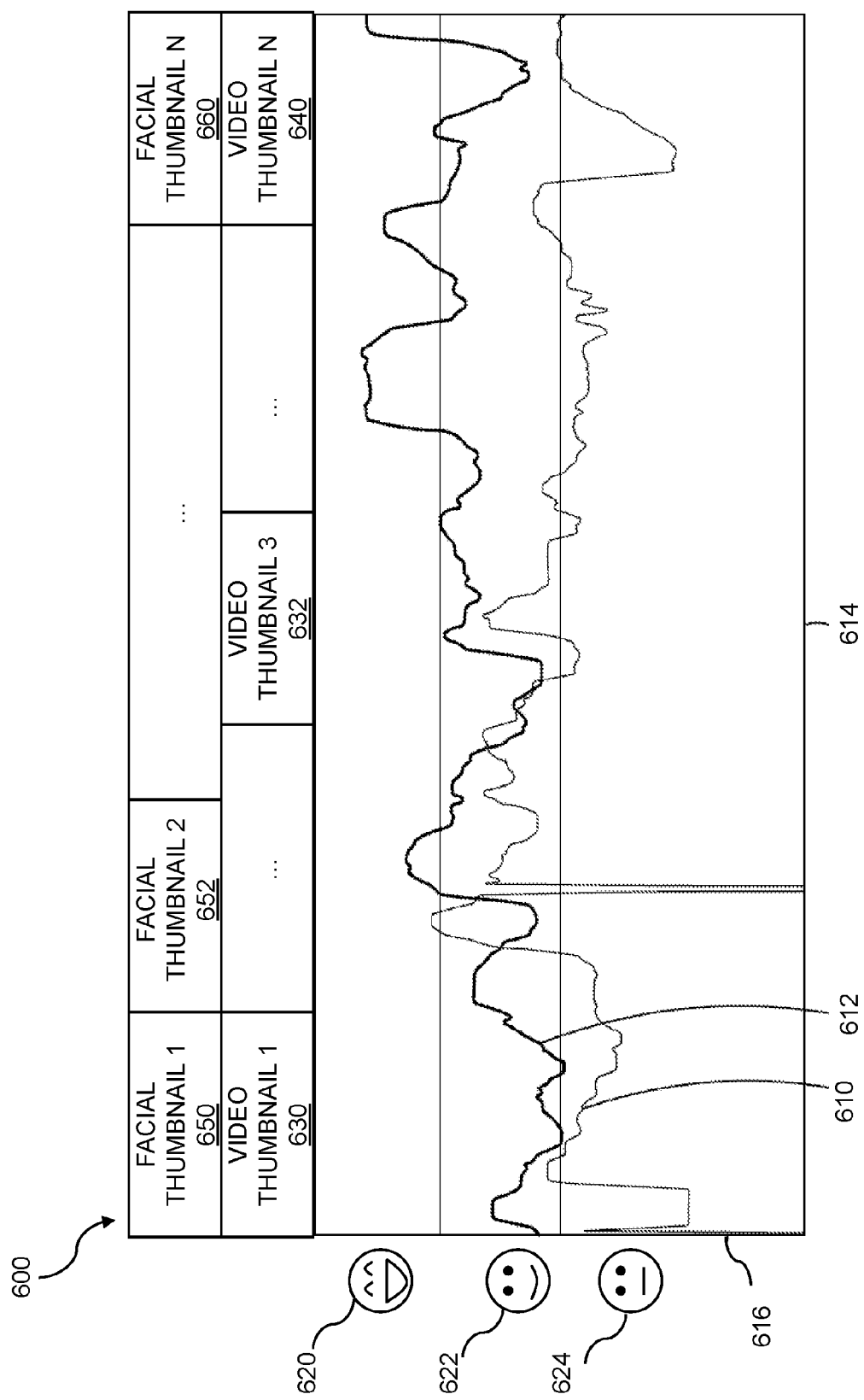
FIG. 6 is a graphical representation for displaying aggregated affect.

FIG. 6 is an example graphical representation for displaying affect based on mental state analysis along with an aggregated result from a group of people. The graphical representation 600 can be displayed on a web page, a web enabled application, a dashboard, or another type of electronic display representation. A graph 610 can be shown for an individual on whom affect data is collected. Another graph 612 can be shown for affect collected on another individual or aggregated affect from multiple people. The mental state analysis can be based on facial image or physiological data collection. In some embodiments, the graph 610 indicates the amount or probability of a smile being observed for the individual. A higher value or point on the graph can indicate a stronger or larger smile. In certain spots, the graph can drop out or degrade when image collection was lost or was not able to identify the face of the person. The probability or intensity of an affect can be given along the y-axis 616, and a timeline can be given along the x-axis 614. The aggregated information can be based on taking the average, median, or another statistical or calculated value based on the information collected from a group of people. In some embodiments, combination of the aggregated mental state information is accomplished using computational aggregation.

In some embodiments, graphical smiley face icons 620, 622, and 624 are shown, providing an indication of the amount of a smile or another facial expression. A first, very broad smiley face icon 620 can indicate a very large smile being observed, a second normal smiley face icon 622 can indicate a smile being observed, and a third face icon 624 can indicate no smile. The icons can correspond to a region on the y-axis 616 that indicate the probability or intensity of a smile.

A set of facial thumbnail images related to the selected graph or graphs, such as Facial Thumbnail 1 650 and Facial Thumbnail 2 652, through Facial Thumbnail N 660, can be shown above or below the graph and can be displayed with a timeline or another parameter along the x-axis 614. The thumbnails can show a graphic "storyboard" of the facial rendering. The storyboard can assist a user in identifying a particular scene or location within the facial rendering. Some embodiments do not include thumbnails or have a single thumbnail associated with the facial rendering, while various other embodiments have thumbnails of equal length and others have thumbnails of differing lengths. In some embodiments, the start and/or end of the thumbnails is determined based on changes in the captured viewer mental states associated with the rendering, or it is based on particular points of interest in the video rendering. Thumbnails of one or more viewers can be shown along a timeline 614 or another parameter. The thumbnails of viewers can include peak expressions, expressions at key points in the video rendering, key points in the graphs, etc.

A set of video thumbnail images comprising scenes from the video for the selected graph or graphs, such as Video Thumbnail 1 630 and Video Thumbnail 2 632, through Video Thumbnail N 640, can be shown above or below the graph and can be displayed with a timeline or another parameter along the x-axis 614. The thumbnails can show a graphic "storyboard" of the video rendering. This storyboard can assist a user in identifying a particular scene or location within the video rendering. Some embodiments do not include thumbnails or have a single thumbnail associated with the rendering, while various other embodiments have thumbnails of equal length, while others have thumbnails of differing lengths. In some embodiments, the start and/or end of the thumbnails is determined based on changes in the captured viewer mental states associated with the rendering, or it is based on particular points of interest in the video rendering.

Figure 7:
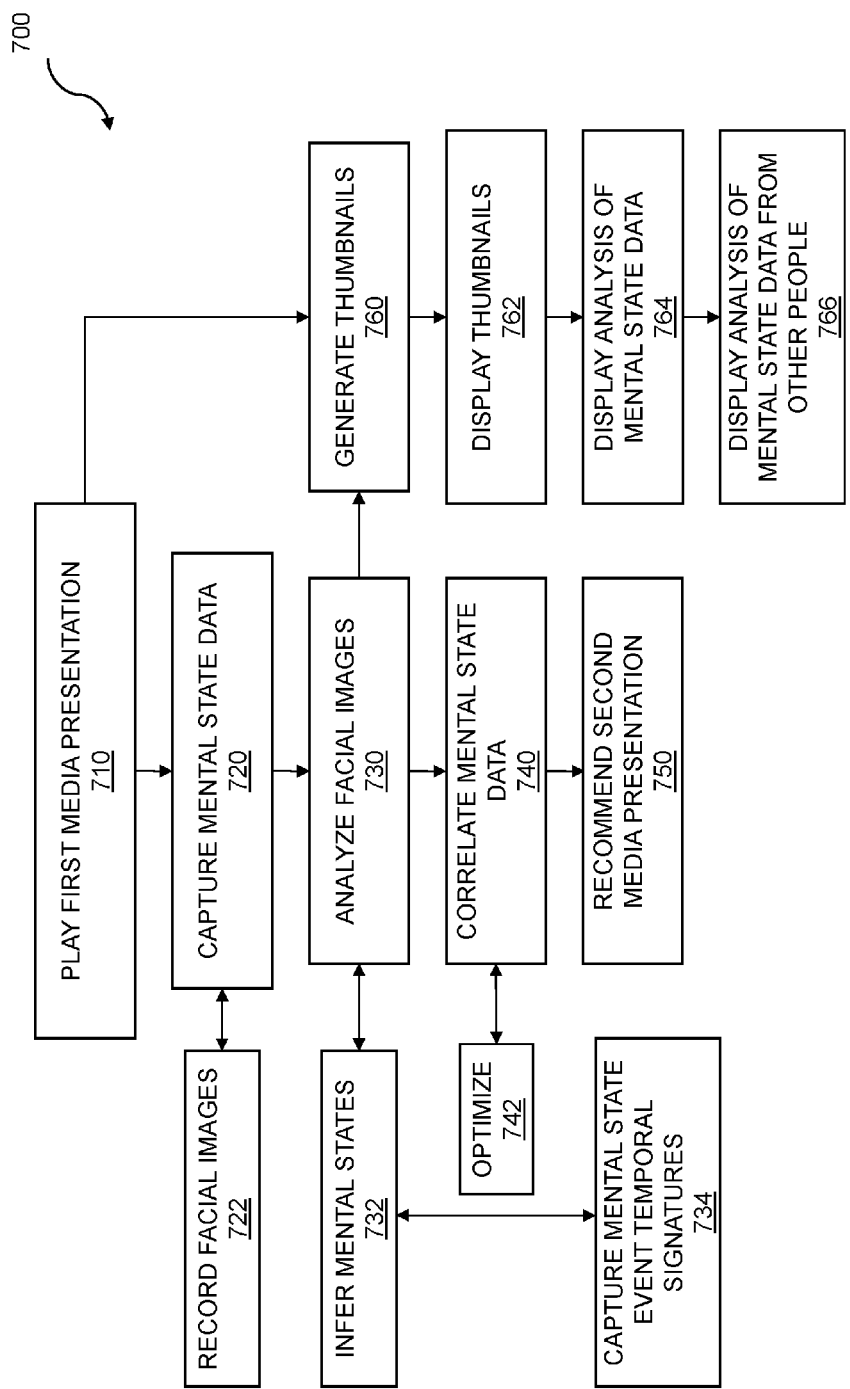
FIG. 7 is a flow diagram for affect-based recommendations.

FIG. 7 is a flow diagram for affect-based recommendations. A flow 700 describes a computer-implemented method for affect-based recommendations. The flow 700 begins with playing a first media presentation 710 to an individual. The first media presentation can be one of a group consisting of a movie, a television show, a web series, a webisode, a video, a video clip, an electronic game, an e-book, and an e-magazine, or another media object. The first media presentation can include a YouTube™ video, a Vimeo™ video, or a Netflix™ video. The first media presentation can be played on a web-enabled interface or another electronic display interface. The web-enabled interface can include a web page. The playing of the first media presentation can be done on a mobile device. The flow 710 continues with capturing mental state data 720 for the individual while the first media presentation is played. The mental state data collected can include physiological data, facial data, actigraphy data, and the like. The capturing of mental state data can further comprise recording facial images 722. Capture of the facial image can be realized by a webcam or another camera. The playing of the first media presentation can be done on a mobile device and the recording of the facial images can also be done with the mobile device. The recording of facial images 722 with the mobile device can be part of the capturing of mental state data 720. The flow 700 further comprises analyzing the facial images 730 for a facial expression. The facial expression can include a smile or a brow furrow. The analyzing facial images can further comprise using the facial images to infer mental states 732. The mental states can include frustration, confusion, disappointment, hesitation, cognitive overload, focusing, being engaged, attending, boredom, exploration, confidence, trust, delight, satisfaction, valence, skepticism, happiness, and the like. The inferring mental states 732 can include capturing a plurality of mental state event temporal signatures 734. The inferring of mental states can be based on the mental state data which was collected and analysis of the video facial data. In embodiments, this analysis of the video facial data is for at least brow furrows.

Clustering be used to include grouping of similar expressions and the mental state event temporal signature can include a time duration and a peak intensity for expressions. In some embodiments, the mental state event temporal signature also includes a shape showing the transition of the intensity. Clustered expressions resulting from the analyzed data can include smiling, smirking, brow furrowing, and so on. The signature for the event can be based on various statistical, mathematical, or other measures. In particular, the event can be characterized by a change in facial expression over time. Of particular interest are rise and hold times, which pertain to how quickly the facial expression formed, and how long it remained. For example, if someone quickly smiles (e.g. within 500 milliseconds), the rise time can be considered short. Whereas if someone gradually smiles with increasing intensity over several seconds, the rise time is longer. Another measure is how long the person continued with the smile, or another expression of interest, based on the stimulus. The signature can include an emotion, in that the identified signature can show collective or individual emotional response to external stimuli. Any emotion can be included in the signature for the event, including one or more of humor, sadness, poignancy, and mirth. Other emotions such as affection, confidence, depression, euphoria, distrust, hope, hysteria, passion, regret, surprise, and zest can also be included. As previously noted, the signature can include time duration information on facial expressions such as a rise time, a fall time, a peak time, and so on, for various expressions. The signature can also include a peak intensity for expressions. The peak intensity can range from a weakest trace to a maximum intensity as defined by a predetermined scale, such as the AU intensity scale. The rating of the intensity can be based on an individual person, on a group of people, and so on. The signature can include a shape for an intensity transition from low intensity to a peak intensity, thus quantifying facial expression transitions as part of the signature. For example, the shape for a low-to-peak intensity transition can indicate a rate at which the transition occurred, whether the peak intensity was sharp or diffuse, and so on. Conversely, the signature can include a shape for an intensity transition from a peak intensity to low intensity as another valuable quantifier of facial expressions. As above, the shape of the peak-to-low intensity transition can indicate a rate at which the transition occurred along with various other useful characteristics relating to the transition. The determining can also include generating other signatures for other events based on the analyzing, or as a result of the analyzing. The other signatures can relate to secondary expressions and can be generated to clarify nuances in a given signature. Returning to the previously mentioned example of a comedic performance, a signature can be determined for a certain type of comedic performance, but in some situations, it might prove helpful to generate further signatures for certain audiences watching a certain instance of the comedic performance. That is, while a plurality of people is watching a comedic performance that already had a signature defined, a second signature can be generated on the group to define a new subgenre of comedic performance, for example.

The mental state event temporal signatures can indicate a collective mental state of a group of people over a period of time as the group experiences an event. For example, the group of people might be asked to view a video. During the course of the video, the mental state of the group of people can be assessed, and a signature can be obtained. For example, the signature can indicate a smile intensity that can correlate to a particular point in the video that the subjects are viewing. In this way, an event can be abstracted to one or more signatures comprising mental states which occur over time. The mental state event temporal signature(s) can be used for analysis. The mental state event temporal signature(s) can be used for correlating mental state data. The flow 700 can include matching a first event signature against the captured mental state data 720. Thus, embodiments include matching a first event signature, from the plurality of mental state event signatures, against the mental state data that was captured. Components of mental state event temporal signatures can include a peak intensity value, a difference between a trough and a peak value, a rate of expression change rising towards the peak or descending from the peak, a duration of intensity, and so on. In embodiments, the following signature attributes are tracked: Event Height (maximum value), Event Length (duration between onset and offset), Event Rise (increase from onset to peak), Event Decay (decrease from peak to next offset), Rise Speed (gradient of event rise), and Decay Speed (gradient of event decay). Signature attributes can be used to determine if a significant event occurred and to help determine the intensity and duration of the event. In embodiments, mental state event temporal signatures are identified by determining the length of time between adjacent local minima of a facial expression probability curve.

The flow 700 continues with correlating the mental state data 740 which was captured for the individual to mental state data collected from other people who experienced the first media presentation. The correlating can include identifying similar likes and dislikes as well as similar various other mental states. In some embodiments, distributions of responses to various videos are correlated, while in other embodiments, differences are correlated, such as, for example, identifying maximally dissimilar responses. Maximally dissimilar can refer to complete opposites, such as a smile vs. a frown or happiness vs. sadness. But maximally dissimilar can also refer to observing differing affect that is unexpected, while not necessarily opposite. For example, a sad video scene could, as expected, elicit a response of sadness. It could also elicit a response of nervous laughing by someone who is unable to cope with the depth of emotion being displayed. However, it could also elicit a non-response, as in the case of a person who tends to be stoic and unexpressive. In this case, the expected response of sadness can be considered maximally dissimilar to a non-response. Furthermore, the unexpected non-response can be considered maximally dissimilar to a nervous laugh response. Many other such examples of non-intuitive maximally dissimilar responses exist. In some embodiments, certain mental states are identified as being similar, while others are identified as being dissimilar during part of the correlation. The flow 700 can include optimizing 742 the media presentation based on the mental state data. The optimizing 742 can include modifying content or recommending changes in content, such as eliminating scenes, reducing certain material, or emphasizing certain actors. In embodiments, the media presentation includes a mixture of advertising and content. The optimizing 742 can select one or more advertisements to be interspersed with the content and can also include ordering one or more advertisements to be interspersed with the content. Additionally, the optimizing 742 can include selecting times within the content for playing the one or more advertisements. The optimizing 742 can include identifying portions of an advertisement that are removed to form a shortened advertisement.

The flow 700 includes recommending a second media presentation 750 to the individual based on the mental state data which was captured for the individual. The recommending the second media presentation to the individual can be based on the correlating between the individual and the other people. The second media presentation can be one of a group consisting of a movie, a television show, a web series, a webisode, a video, a video clip, an electronic game, an e-book, and an e-magazine, and the like. The second media presentation can include a YouTube™ video, a Vimeo™ video, or a Netflix™ video.

The flow 700 can further comprise generating a set of thumbnails 760 for the first media presentation which was played and displaying the set of thumbnails 762 on a second web-enabled interface or digital display along with an analysis of the mental state data from the individual 764. The set of thumbnails can comprise scenes from the first media presentation. The selection of the thumbnail from the set of thumbnails can be based on facial expressions. The set of thumbnails can be generated automatically and can include removing a frame from the set of thumbnails based on a dark threshold. Another frame can be used in place of the frame that was removed. The flow 700 can further comprise displaying an analysis of the mental state data from the other people 766. Various steps in the flow 700 may be changed in order, repeated, omitted, or the like without departing from the disclosed inventive concepts. Various embodiments of the flow 700 may be included in a computer program product embodied in a non-transitory computer readable medium that includes code executable by one or more processors.

Figure 8:
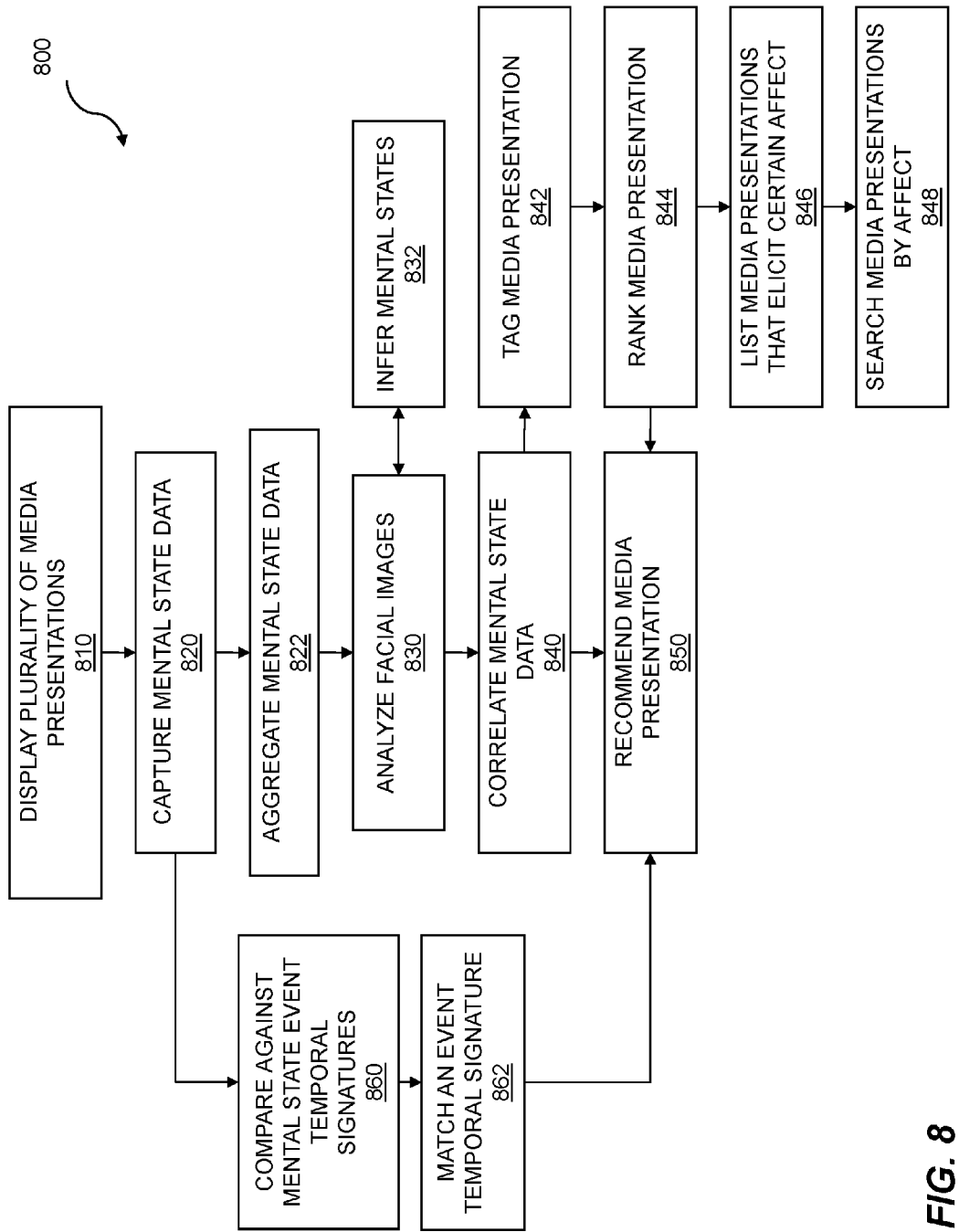
FIG. 8 is a flow diagram for affect-based video ranking.

FIG. 8 is a flow diagram for affect-based video ranking and shows a flow 800 which describes a computer-implemented method for affect-based ranking. The flow 800 begins with displaying a plurality of media presentations 810 to a group of people. The plurality of media presentations can include videos. The plurality of videos can include YouTube™ videos, Vimeo™ videos, or Netflix™ videos. Further, the plurality of media presentations can include one of a group consisting of a movie, a movie trailer, a television show, a web series, a webisode, a video, a video clip, an advertisement, a music video, an electronic game, an e-book, and an e-magazine. The flow 800 continues with capturing mental state data 820 from the group of people while the plurality of media presentations is displayed. Thus, mental state data can be captured from multiple people. The affect data can include facial images. In some embodiments, the playing of the media presentations is done on a mobile device and the recording of the facial images is done with the mobile device. The flow 800 includes aggregating the mental state data 822 from the multiple people. The flow 800 further comprises analyzing the facial images 830 for a facial expression. The facial expression can include a smile or a brow furrow. The flow 800 can further comprise using the facial images to infer mental states 832. The mental states can include one of a group consisting of frustration, confusion, disappointment, hesitation, cognitive overload, focusing, being engaged, attending, boredom, exploration, confidence, trust, delight, valence, skepticism, satisfaction, and the like.

The flow 800 includes correlating the mental state data 840 captured from the group of people who have viewed the plurality of media presentations and had their mental state data captured. The plurality of videos viewed by the group of people can have some common videos seen by each of the people in the group of people. In some embodiments, the plurality of videos does not include an identical set of videos. The flow 800 can continue with tagging the plurality of media presentations 842 with mental state information based on the mental state data which was captured. In some embodiments, the affect information is simply the affect data, while in other embodiments, the affect information is the inferred mental states. In still other embodiments, the affect information is the results of the correlation. The flow 800 can continue with ranking the media presentations 844 relative to another media presentation based on the mental state data which was collected. The ranking can be for an individual based on the mental state data captured from the individual. The ranking can be based on anticipated preferences for the individual. In some embodiments, the ranking of a first media presentation relative to another media presentation is based on the mental state data which was aggregated from multiple people. The ranking can also be relative to media presentations previously stored with affect information. The ranking can include ranking a video relative to another video based on the mental state data which was captured. The flow 800 can further comprise displaying the videos which elicit a certain affect 846. The certain affect can include one of a group consisting of smiles, engagement, attention, interest, sadness, liking, disliking, and so on. The ranking can further comprise displaying the videos which elicited a larger number of smiles. As a result of ranking, the media presentations can be sorted based on which videos are the funniest, which are the saddest, which generate the most tears, or which engender some other response. The flow 800 can further comprise searching through the videos based on a certain affect data 848. A search 848 can identify videos which are very engaging, funny, sad, poignant, or the like.

The flow 800 includes comparing the mental state data that was captured for the individual against a plurality of mental state event temporal signatures 860. In embodiments, multiple mental state event temporal signatures have been obtained from previous analysis of numerous people. The mental state event temporal signatures can include information on rise time to facial expression intensity, fall time from facial expression intensity, duration of a facial expression, and so on. In some embodiments, the mental state event temporal signatures are associated with certain demographics, ethnicities, cultures, etc. The mental state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The mental state event temporal signatures can be used to identify liking or satisfaction with a media presentation. The mental state event temporal signatures can be used to correlate with appreciating a second media presentation. The flow 800 can include matching a first event signature 862, from the plurality of mental state event temporal signatures, against the mental state data that was captured. The matching can include identifying similar aspects of the mental state event temporal signature such as rise time, fall time, duration, and so on. The matching can include matching a series of facial expressions described in mental state event temporal signatures. In some embodiments, a second mental state event temporal signature is used to identify a sequence of mental state data being expressed by an individual.

The flow 800 includes recommending a second media presentation 850 to an individual based on the affect data that was captured and based on the ranking. The recommending the second media presentation to the individual is further based on the comparing of the mental state data to the plurality of mental state event temporal signatures. The second media presentation can be one of a group consisting of a movie, a movie trailer, a television show, a web series, a webisode, a video, a video clip, an advertisement, a music video, an electronic game, an e-book, and an e-magazine. The recommending the second media presentation can be further based on the matching of the first event signature. The recommending can be based on the similarity of mental states that were expressed. The recommending can be based on a numerically quantifiable determination of satisfaction or appreciation of the first media and an anticipated numerically quantifiable satisfaction or appreciation of second first media presentation.

Based on the mental states, recommendations to or from an individual can be provided. One or more recommendations can be made to the individual based on mental states, affect, or facial expressions. A correlation can be made between one individual and others with similar affect exhibited during multiple videos. The correlation can include a record of other videos, games, or other experiences, along with their affect. Likewise, a recommendation for a movie, video, video clip, webisode or another activity can be made to an individual based on their affect. Various steps in the flow 800 may be changed in order, repeated, omitted, or the like without departing from the disclosed inventive concepts. Various embodiments of the flow 800 may be included in a computer program product embodied in a non-transitory computer readable medium that includes code executable by one or more processors.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or another camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

In some embodiments, a high frame rate camera is used. A high frame rate camera has a frame rate of 60 frames per second or higher. With such a frame rate, micro expressions can also be captured. Micro expressions are very brief facial expressions, lasting only a fraction of a second. They occur when a person either deliberately or unconsciously conceals a feeling.

In some cases, micro expressions happen when people have hidden their feelings from themselves (repression) or when they deliberately try to conceal their feelings from others. Sometimes the micro expressions might only last about 50 milliseconds. Hence, these expressions can go unnoticed by a human observer. However, a high frame rate camera can be used to capture footage at a sufficient frame rate such that the footage can be analyzed for the presence of micro expressions. Micro expressions can be analyzed via action units as previously described, with various attributes such as brow raising, brow furls, eyelid raising, and the like. Thus, embodiments analyze micro expressions that are easily missed by human observers due to their transient nature.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include such items as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. For example, the AUs can be used to recognize emotions experienced by the observed person. Emotion-related facial actions can be identified using the emotional facial action coding system (EM-FACS) and the facial action coding system affect interpretation dictionary (FACSAID), for example. For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness, for example. The automated systems can be based on a probability estimate from one or more classifiers, where the probabilities can correlate with an intensity of an AU or an expression. The classifiers can be used to identify into which of a set of categories a given observation can be placed. For example, the classifiers can be used to determine a probability that a given AU or expression is present in a given frame of a video. The classifiers can be used as part of a supervised machine learning technique where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. For example, the image can be adjusted by flipping the image around a vertical line through the middle of a face in the image. The symmetry plane of the image can be determined from the tracker points and landmarks of the image.

In an embodiment, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis.

Figure 9:
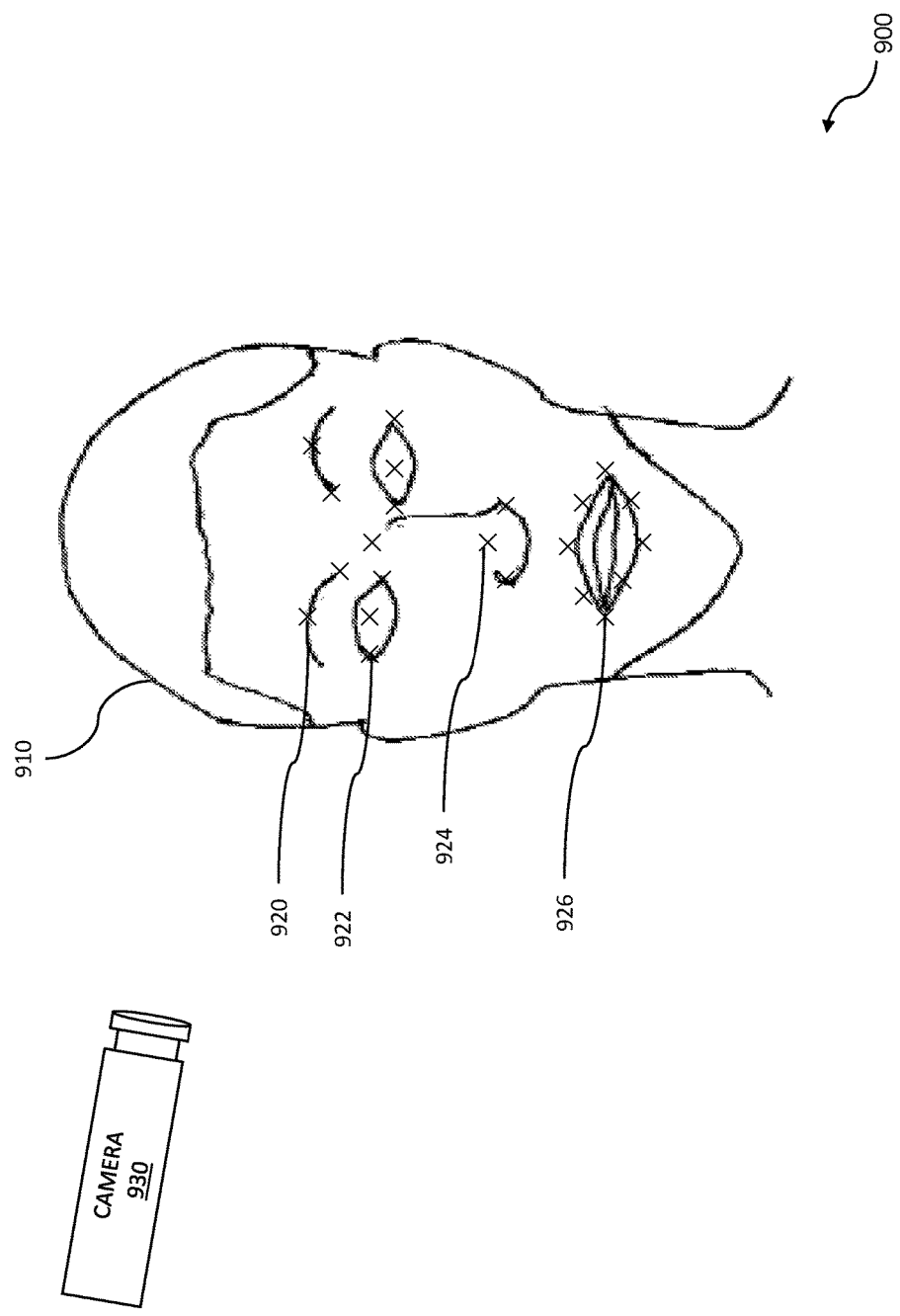
FIG. 9 shows example facial data collection including landmarks.

FIG. 9 shows a diagram 900 illustrating example facial data collection including landmarks. A face 910 can be observed using a camera 930 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 930 relative to the face 910, the number of cameras used, the illumination of the face, etc. For example, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks can be identified from the facial data that is captured. The facial landmarks that are identified can be analyzed to identify facial action units. For example, the action units that can be identified include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures).

Figure 10:
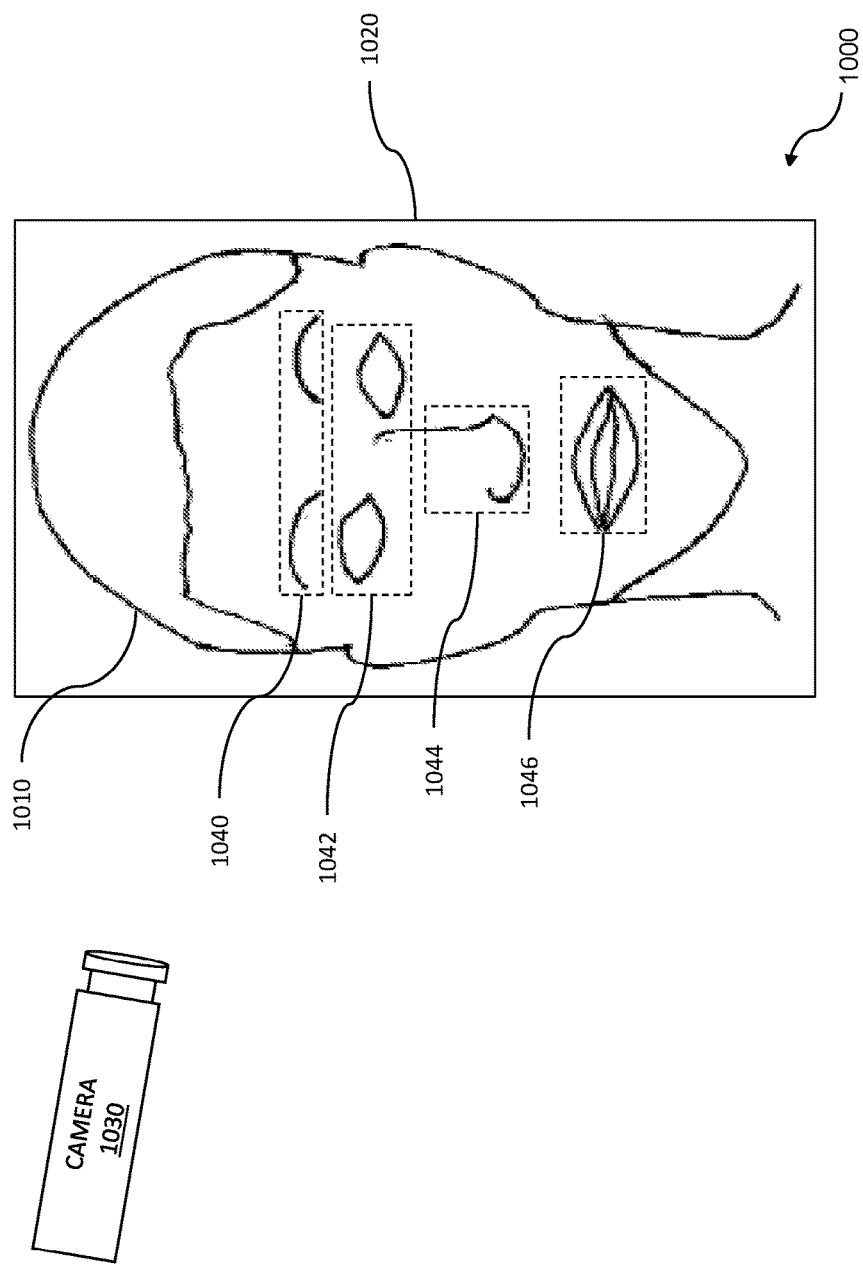
FIG. 10 shows example facial data collection including regions.

FIG. 10 shows example facial data collection including regions. The collecting of facial data including regions can be performed for data collected from a remote computing device. The facial data including regions can be collected from people as they interact with the Internet. Various regions of a face can be identified and used for a variety of purposes including facial recognition, facial analysis, and so on. The collecting of facial data including regions can be based on sub-sectional components of a population. The sub-sectional components can be used with performing the evaluation of content of the face, identifying facial regions, etc. The sub-sectional components can be used to provide a context. Facial analysis can be used to determine, predict, estimate, etc. mental states, emotions, and so on of a person from whom facial data can be collected. The one or more emotions that can be determined by the analysis can be represented by an image, a figure, an icon, etc. The representative icon can include an emoji. One or more emoji can be used to represent a mental state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1000, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1010 can be observed using a camera 1030, a sensor, a combination of cameras and/or sensors, and so on. The camera 1030 can be used to collect facial data that can be used to determine that a face is present in an image. When a face is present in an image, a bounding box 1020 can be placed around the face. Placement of the bounding box around the face can be based on detection of facial landmarks. The camera 1030 can be used to collect from the bounding box 1020 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1030 relative to the face 1010, the number of cameras and/or sensors used, the illumination of the face, any obstructions to viewing the face, and so on.

The facial regions that can be collected by the camera 1030, sensor, or combination of cameras and/or sensors can include any of a variety of facial features. The facial features that can be included in the facial regions that are collected can include eyebrows 1040, eyes 1042, a nose 1044, a mouth 1046, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1030, a sensor, or a combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth potion of skin such as a smooth portion of a check. A gradient in a facial region can include values assigned to local skin texture, shading, etc. A gradient can be used to encode, for instance, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be included in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVM), logistic regression, classification trees, and so on. By way of example, consider facial features that can include the eyebrows 1040. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate the person from whom the facial data was collected is annoyed, confused, unhappy, and so on. In another example, consider facial features that can include a mouth 1046. One or more classifiers can be used to analyze the facial region that can include the mouth to determine a probability for either a presence or an absence of mouth edges turned up to form a smile. Multiple classifiers can be used to determine one or more facial expressions.

Figure 11:
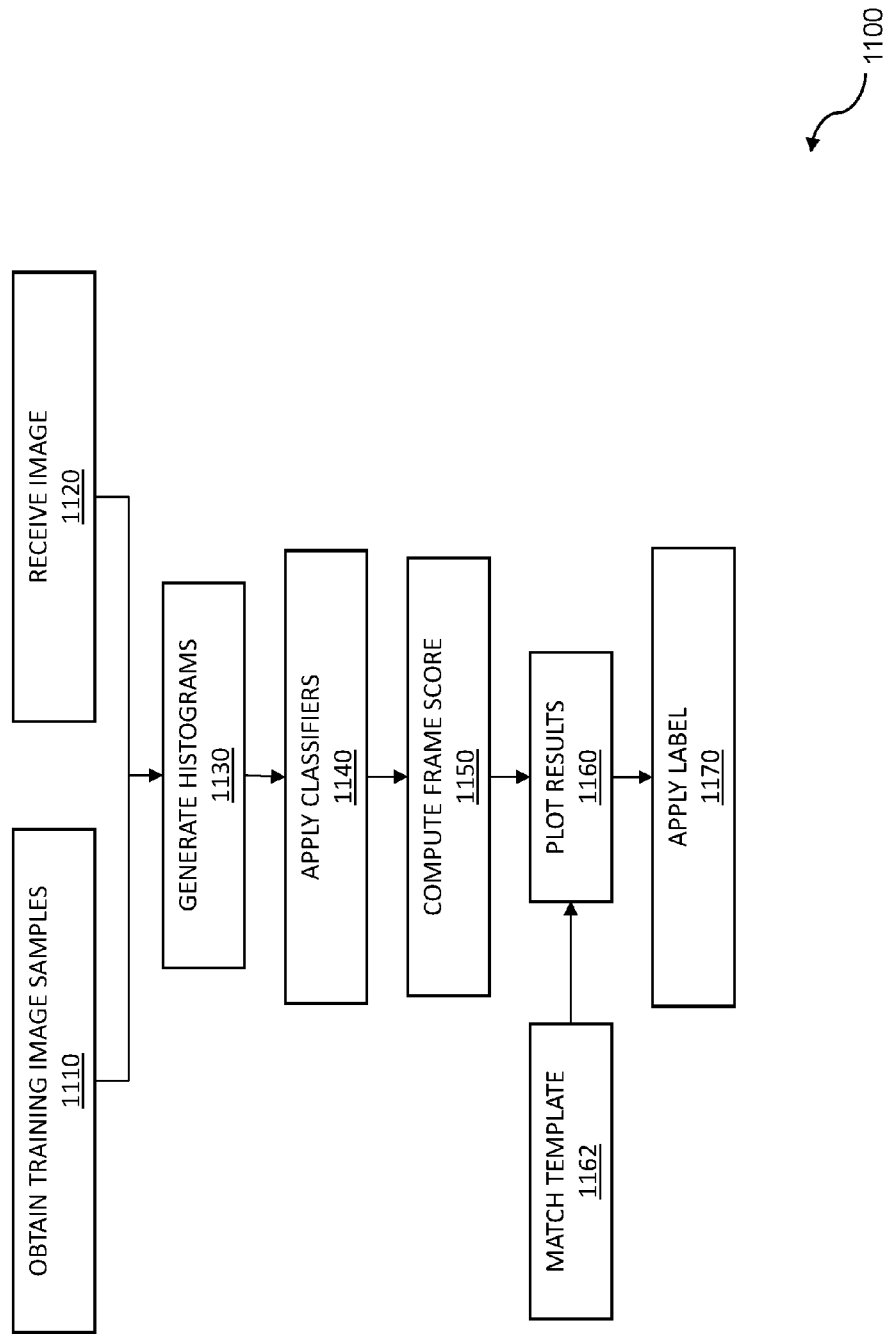
FIG. 11 is a flow diagram for detecting facial expressions.

FIG. 11 is a flow diagram for detecting facial expressions. The flow 1100 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU) where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1100 begins by obtaining training image samples 1110. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, such as the camera 230 from FIG. 2, for example. The flow 1100 continues with receiving an image 1120. The image 1120 can be received from a camera, such as the camera 230 from FIG. 2, for example. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image 1120 that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1100 continues with generating histograms 1130 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1100 continues with applying classifiers 1140 to the histograms. The classifiers can be used to estimate probabilities where the probabilities can correlate with an intensity of an AU or an expression. The choice of classifiers used is based on the training of a supervised learning technique to identify facial expressions, in some embodiments. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1100 continues with computing a frame score 1150. The score computed for an image, where the image can be a frame from a video, can be used to determine the presence of a facial expression in the image or video frame. The score can be based on one or more versions of the image 1120 or manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1100 continues with plotting results 1160. The results that are plotted can include one or more scores for one or more frames computed over a given time t. For example, the plotted results can include classifier probability results from analysis of HoGs for a sequence of images and video frames. The plotted results can be matched with a template 1162. The template can be temporal and can be represented by a centered box function or another function. A best fit with one or more templates can be found by computing a minimum error. Other best-fit techniques can include polynomial curve fitting, geometric curve fitting, and so on. The flow 1100 continues with applying a label 1170. The label can be used to indicate that a particular facial expression has been detected in the one or more images or video frames which constitute the image 1120. For example, the label can be used to indicate that any of a range of facial expressions has been detected, including a smile, an asymmetric smile, a frown, and so on. Various steps in the flow 1100 may be changed in order, repeated, omitted, or the like without departing from the disclosed concepts. Various embodiments of the flow 1100 may be included in a computer program product embodied in a non-transitory computer readable medium that includes code executable by one or more processors.

Figure 12:
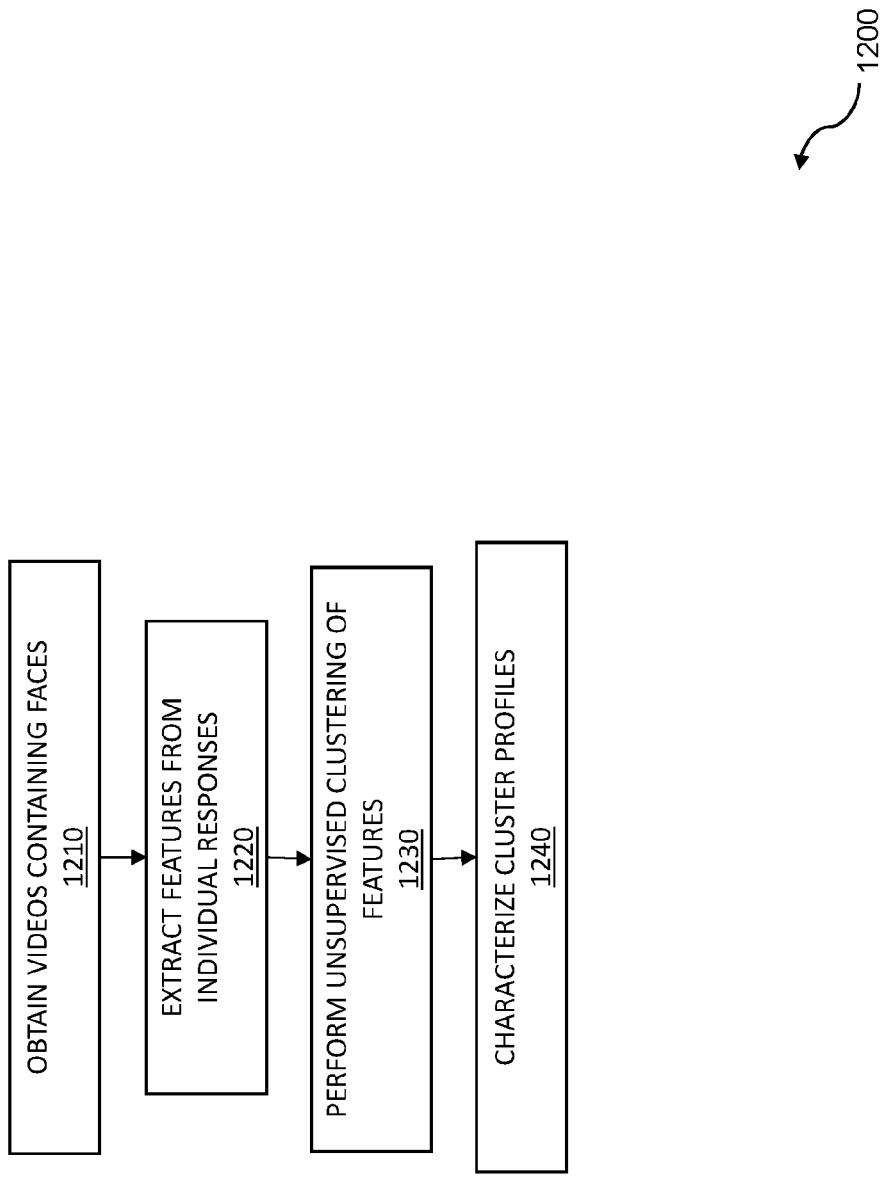
FIG. 12 is a flow diagram for large-scale clustering of facial events.

FIG. 12 is a flow diagram for large-scale clustering of facial events. As discussed above, collection of facial video data from one or more people can include a web-based framework. The web-based framework can be used to collect facial video data from, for example, large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on. The flow 1200 begins with obtaining videos containing faces 1210. The videos can be obtained using one or more cameras, where the cameras can include a webcam coupled to one or more devices employed by the one or more people using the web-based framework. The flow 1200 continues with extracting features from the individual responses 1220. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1200 continues with performing unsupervised clustering of features 1230. The unsupervised clustering can be based on an event. The features can be extracted from compared mental state data. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1200 continues with characterizing cluster profiles 1240. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared to various demographic groups, where the groups can be formed based on geographic location, age, ethnicity, gender, and so on. Various steps in the flow 1200 may be changed in order, repeated, omitted, or the like without departing from the disclosed concepts. Various embodiments of the flow 1200 may be included in a computer program product embodied in a non-transitory computer readable medium that includes code executable by one or more processors.

Figure 13:
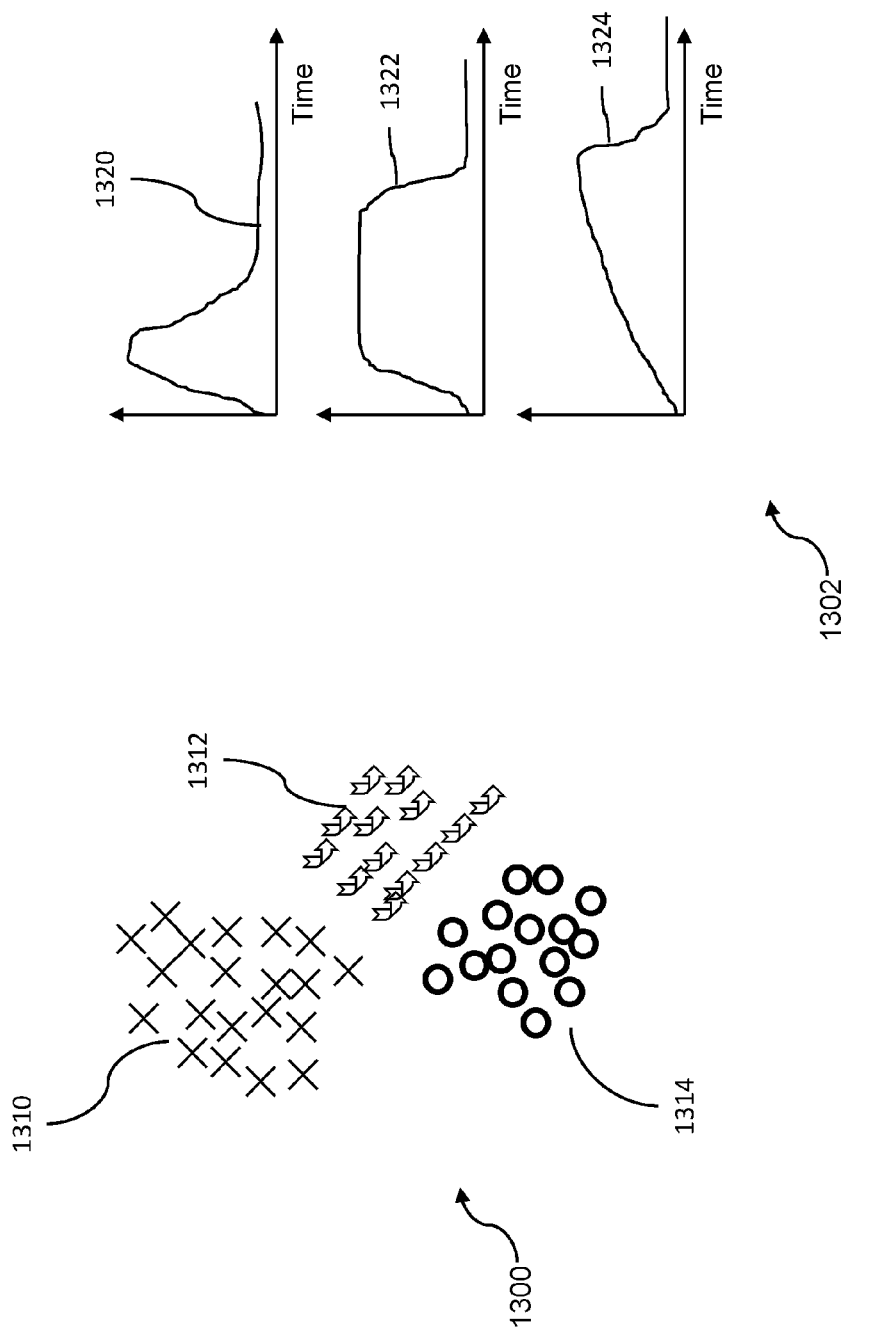
FIG. 13 shows example unsupervised clustering of features and characterizations of cluster profiles.

FIG. 13 shows example unsupervised clustering of features and characterization of cluster profiles. This clustering can be used to generate or identify mental state event temporal signatures. Features including samples of facial data can be clustered using unsupervised clustering. Various clusters can be formed, which include similar groupings of facial data observations. The example 1300 shows three clusters: clusters 1310, 1312, and 1314. The clusters can be based on video collected from people who have opted-in to video collection. When the data collected is captured using a web-based framework, then the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

Cluster profiles 1302 can be generated based on the clusters that can be formed from unsupervised clustering, with time shown on the x-axis and intensity or frequency shown on the y-axis. The cluster profiles can be based on captured facial data including facial expressions, for example. The cluster profile 1320 can be based on the cluster 1310, the cluster profile 1322 can be based on the cluster 1312, and the cluster profile 1324 can be based on the cluster 1314. The cluster profiles 1320, 1322, and 1324 can be based on smiles, smirks, frowns, or any other facial expression. Emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information as described above.

Figures 14A, 14B:
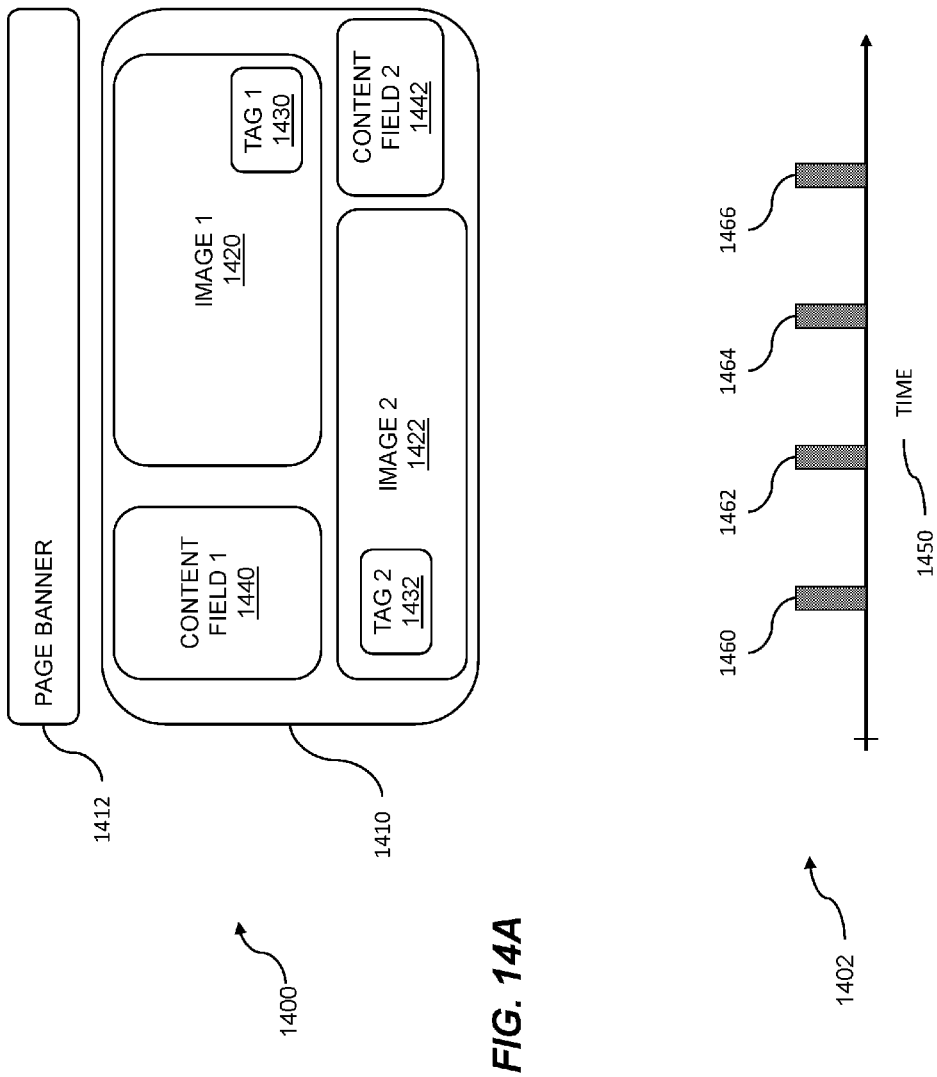
FIG. 14A shows example tags embedded in a webpage.
FIG. 14B shows example invoking tags for the collection of images.

FIG. 14A shows example tags embedded in a webpage. A webpage 1400 can include a page body 1410, a page banner 1412, and so on. The page body can include one or more objects, where the objects can include text, images, videos, audio, and so on. The example page body 1410 shown includes a first image, image 1 1420; a second image, image 2 1422; a first content field, content field 1 1440; and a second content field, content field 2 1442. In practice, the page body 1410 can contain any number of images and content fields, and can include one or more videos, one or more audio presentations, and so on. The page body can include embedded tags, such as tag 1 1430 and tag 2 1432. In the example shown, tag 1 1430 is embedded in image 1 1420, and tag 2 1432 is embedded in image 2 1422. In embodiments, any number of tags are imbedded. Tags can also be imbedded in content fields, in videos, in audio presentations, etc. When a user mouses over a tag or clicks on an object associated with a tag, the tag can be invoked. For example, when the user mouses over tag 1 1430, tag 1 1430 can then be invoked. Invoking tag 1 1430 can include enabling a camera coupled to a user's device and capturing one or more images of the user as the user views a media presentation (or digital experience). In a similar manner, when the user mouses over tag 2 1432, tag 2 1432 can be invoked. Invoking tag 2 1432 can also include enabling the camera and capturing images of the user. In other embodiments, other actions are taken based on invocation of the one or more tags. For example, invoking an embedded tag can initiate an analysis technique, post to social media, award the user a coupon or another prize, initiate mental state analysis, perform emotion analysis, and so on.

FIG. 14B shows example tag invoking for the collection of images. As stated above, a media presentation can be a video, a webpage, and so on. A video 1402 can include one or more embedded tags, such as a tag 1460, another tag 1462, a third tag 1464, a fourth tag 1466, and so on. In practice, any number of tags can be included in the media presentation. The one or more tags can be invoked during the media presentation. The collection of the invoked tags can occur over time as represented by a timeline 1450. When a tag is encountered in the media presentation, the tag can be invoked. For example, when the tag 1460 is encountered, invoking the tag can enable a camera coupled to a user's device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1460 does not enable the camera nor capture images of the user during the media presentation. The user can indicate an opt-in for certain types of participation, where opting-in can be dependent on specific content in the media presentation. For example, the user could opt-in to participation in a study of political campaign messages and not opt-in for an advertisement study. In this case, tags that are related to political campaign messages and that enable the camera and image capture when invoked would be embedded in the media presentation. However, tags imbedded in the media presentation that are related to advertisements would not enable the camera when invoked. Various other situations of tag invocation are possible.

Figure 15:
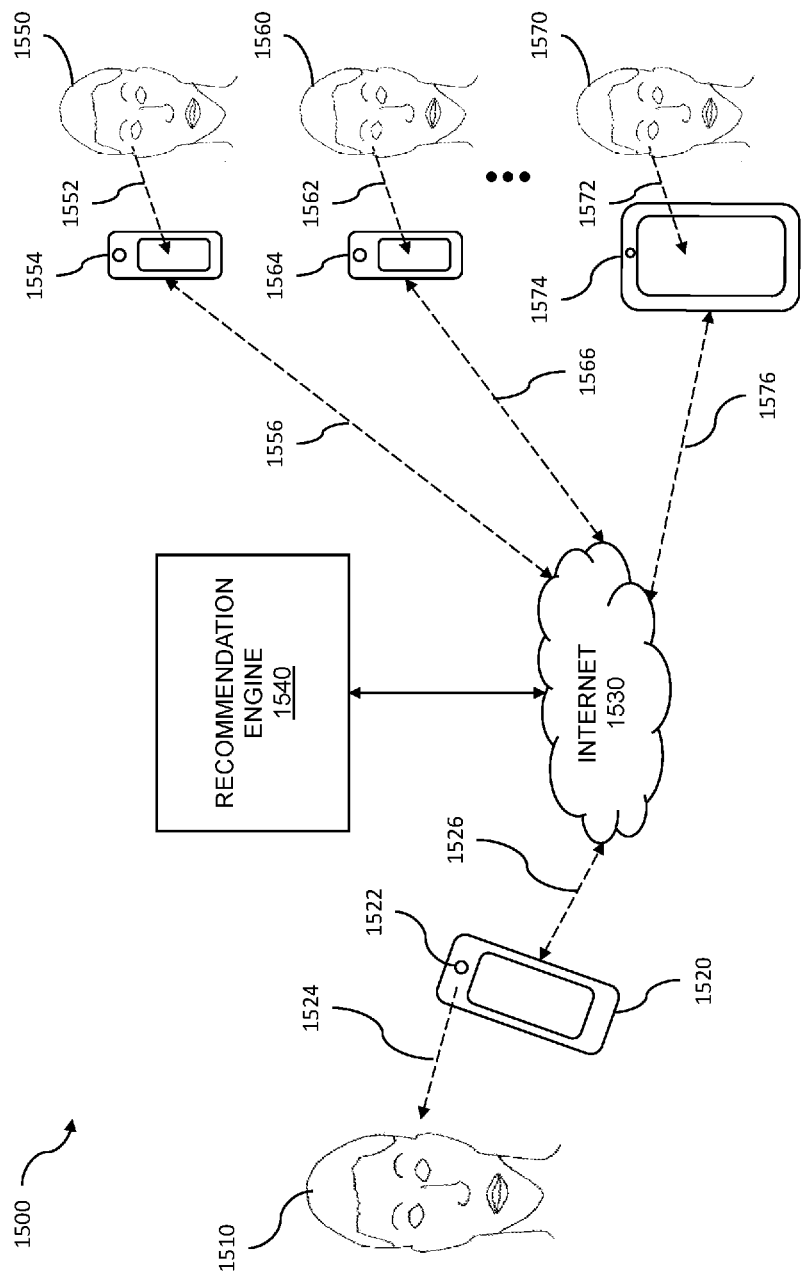
FIG. 15 shows an example live-streaming social video scenario.

FIG. 15 shows an example live-streaming social video scenario. Live-streaming video is an example of one-to-many social media where video can be sent over the Internet from one person to a plurality of people using a social media app and/or platform. Live-streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcast as and when needed or desirable. Examples of impromptu live-stream videos can range from individuals simply wanting to share experiences with their social media followers, to coverage of breaking news, emergencies, or natural disasters. This latter coverage is known as mobile journalism, or "mo jo", and is becoming increasingly commonplace. "Reporters" can use networked, portable electronic devices to provide mobile journalism content to a plurality of social media followers. Such reporters can be quickly and inexpensively deployed as the need or desire arises.

Several live-streaming social media apps and platforms can be used for transmitting video. One such video social media app is Meerkat™ that can link with a user's Twitter™ account. Meerkat™ enables a user to stream video using a handheld, networked, electronic device coupled to video capabilities. Viewers of the live stream can comment on the stream using tweets that can be seen by and responded to by the broadcaster. Another popular app is Periscope™ that can transmit a live recording from one user to that user's Periscope™ or other social media followers. The Periscope™ app can be executed on a mobile device. The user's followers can receive an alert whenever that user begins a video transmission. Another live-stream video platform is Twitch which can be used for video streaming of video gaming, and broadcasts of various competitions, concerts and other events.

The example 1500 shows a user 1510 broadcasting a video live-stream to one or more people 1550, 1560, 1570, and so on. A portable, network-enabled electronic device 1520 can be coupled to a camera 1522 that is forward facing or front facing. The portable electronic device 1520 can be a smartphone, a PDA, a tablet, a laptop computer, and so on. The camera 1522 coupled to the device 1520 can have a line-of-sight view 1524 to the user 1510 and can capture video of the user 1510. The captured video can be sent to a recommendation engine 1540 using a network link 1526 to the Internet 1530. The network link can be a wireless link, a wired link, and so on. The recommendation engine 1540 can recommend to the user 1510 an app and/or platform that can be supported by the server and can be used to provide a video live-stream to one or more followers of the user 1510. The example 1500 shows three followers of user 1510, followers 1550, 1560, and 1570. Each follower has a line-of-sight view to a video screen on a portable, networked electronic device. In other embodiments, one or more followers follow the user 1510 using any other networked electronic device, including a computer. In the example 1500, the person 1550 has a line-of-sight view 1552 to the video screen of a device 1554, the person 1560 has a line-of-sight view 1562 to the video screen of a device 1564, and the person 1570 has a line-of-sight view 1572 to the video screen of a device 1574. The portable electronic devices 1554, 1564, and 1574 each can be a smartphone, a PDA, a tablet, and so on. Each portable device can receive the video stream being broadcast by the user 1510 through the Internet 1530 using the app and/or platform that can be recommended by the recommendation engine 1540. The device 1554 can receive a video stream using the network link 1556, the device 1564 can receive a video stream using the network link 1566, the device 1574 can receive a video stream using the network link 1576, and so on. The network link can be a wireless link, and wired link, and so on. Depending on the app and/or platform that can be recommended by the recommendation engine 1540, one or more followers, such as followers 1550, 1560, 1570, and so on, can reply to, comment on, and otherwise provide feedback to the user 1510 using their devices 1554, 1564, and 1574 respectively.

As described above, one or more videos of various types including live-streamed videos can be presented to a plurality of users for wide ranging purposes. These purposes can include, but are not limited to, entertainment, education, general information, political campaign messages, social media sharing, and so on. Mental state data can be collected from the one or more users as they view the videos. The collection of the mental state data can be based on a user agreeing to enable a camera that can be used for the collection of the mental state data. The collected mental state data can be analyzed for various purposes. When the mental state data has been collected from a number of users (to enable anonymity), then the aggregated mental state data can be used to provide information on aggregated mental states of the viewers. The aggregated mental states can be used to recommend videos that can include media presentations, for example. For example, the recommendations of videos can be based on videos that are like videos to which a user had a particular mental state response. The recommendations of videos can include videos to which the user might be more likely to have a favorable mental state response, videos that might be enjoyed by the user's social media contacts, videos that might be trending, and so on.

The aggregated mental state data can be represented using a variety of techniques and can be presented to the one or more users. The aggregated mental state data can be presented while the one or more users are viewing the video, and the aggregated mental state data can be presented after the one or more users have viewed the video. The video can be obtained from a server, a collection of videos, a live-stream video, and so on. The aggregated mental state data can be presented to the users using a variety of techniques. For example, the aggregated mental state data can be displayed as colored dots, as graphs, etc. The colored dots, graphs, and so on, can be displayed with the video, embedded in the video, viewed subsequently to viewing the video, or presented in another fashion. The aggregated mental state data can also be used to provide feedback to the originator of the video, where the feedback can include viewer reaction or reactions to the video, receptiveness to the video, effectiveness of the video, etc. The aggregated mental state data can include one of a group consisting of sadness, happiness, frustration, confusion, disappointment, hesitation, cognitive overload, focusing, being engaged, attending, boredom, exploration, confidence, trust, delight, valence, skepticism, satisfaction, and so on. The videos can include live-streamed videos. The videos and the live-streamed videos can be presented along with the aggregated mental state data from the one or more users. The aggregated mental state data, as viewed by the users, can be employed by the same users to determine what mental states are being experienced by other users as all parties view a given video, when those mental states occur, whether those mental states are similar to the one or more mental states experienced by the users, and so on. The viewing of the aggregated mental state data can enable a viewer to experience videos viewed by others, to feel connected to other users who are viewing the videos, to share in the experience of viewing the videos, to gauge the mental states experienced by the users, and so on.

The collecting of mental state data can be performed as one or more users observe the videos described above. For example, a news site, a social media site, a crowd-sourced site, an individual's digital electronic device, etc., can provide the videos. The mental state data can be collected as the one or more users view a given video or live-stream video. The mental state data can be recorded and analyzed. The results of the analysis of the collected mental state data from the one or more users can be displayed to the one or more users following the viewing of the video, for example. For confidentiality reasons, mental state data can be collected from a minimum or threshold number of users before the aggregated mental state data is displayed. One or more users on one or more social media sites can share their individual mental state data and the aggregated mental state data that was collected. For example, a user could share with their Facebook™ friends her or his mental state data results from viewing a particular video. How a user responds to a video can be compared to the responses of their friends, of other users, etc., using a variety of techniques, such as a social graph. For example, the user could track the reactions of her or his friends to a particular video using a Facebook™ social graph. The mental state data can be shared automatically or can be shared manually, as selected by the user. Automatic sharing of mental state data can be based on user credentials, such as logging in to a social media site. A user's privacy can also be enabled using a variety of techniques, including anonymizing a user's mental state data, anonymizing and/or deleting a user's facial data, and so on. Facial tracking data can be provided in real time. In embodiments, the user has full control of playback of a video, a streamed video, a live-streamed video, and so on. That is, the user can pause, skip, scrub, go back, stop, and so on. Recommendations can be made to the user regarding viewing another video. The flow of a user viewing a video can continue from the current video to another video based on the recommendations. The next video can be a streamed video, a live-streamed video, and so on.

In another embodiment, aggregated mental state data can be used to assist a user to select a video, video stream, live-stream video, and so on, that can be considered most engaging to the user. For instance, if there is a user who is interested in a particular type of video stream such as a gaming stream, a sports stream, a news stream, a movie stream, and so on, and that favorite video stream is not currently available to the user, then recommendations can be made to the user based on a variety of criteria to assist in finding an engaging video stream. The user could connect to a video stream that is presenting one or more sports events, but if the stream does not include the stream of the user's favorite, then recommendations can be made to the user based on aggregated mental state data of other users who are ranking or reacting to the one or more sports events currently available. Similarly, if analysis of the mental state data collected from the user indicates that the user is not reacting favorably to a given video stream, then a recommendation can be made for another video stream based on an audience who is engaged with the latter stream.

A given user can choose to participate in collection of mental state data for a variety of purposes. One or more personae can be used to characterize or classify a given user who views one or more videos. The personae can be useful for recommending one or more videos to a user based on mental state data collected from the user, for example. The recommending of one or more videos to the user can be based on aggregated mental state data collected from one or more users with a similar persona. Many personae can be described and chosen based on a variety of criteria. For example, personae can include a demo user, a social sharer, a video viewing enthusiast, a viral video enthusiast, an analytics research, a quantified self-user, a music aficionado, and so on. Any number of personae can be described, and any number of personae can be assigned to a particular user.

A demo user can be a user who is curious about the collection of mental state data and the presentation of that mental state data. The demo user can view any number of videos to experience the mental state data collection and to observe their own social curve, for example. The demo user can view some viral videos to observe an aggregated population. The demo user can be interested in trying mental state data collection and presentation to determine how she or he would use such a technique for their own purposes.

A social sharer can be a user who is enthusiastic about sharing demos and videos with their friends. The friends can be social media friends such as Facebook™ friends, for example. The videos can be particularly engaging, flashy, well-produced, and so on. The social sharer can be interested in the reactions to and the sharing of the video that the social sharer has shared. The social sharer can also compare their own mental states to those of their friends. The social sharer can use the comparison to increase their knowledge of their friends and to gather information about the videos that those friends enjoyed.

A video-viewing enthusiast can be a user who enjoys watching videos and desires to watch more videos. Such a persona can generally stay within the context of a video streaming site, for example. The viewing by the user can be influenced by recommendations that draw the user back to view more videos. When the user finds that the recommendations are desirable, then the user likely can continue watching videos within the streaming site. The video enthusiast can want to find the videos that the user wants to watch as well as the portions of the videos that the user wants to watch.

A viral video enthusiast can be a user who chooses to watch many videos through social media. The social media can include links, shares, comments, etc. from friends of the user, for example. When the user clicks on the link to the video, the user can be connected from the external site to the video site. For example, the user can click a link in Reddit™, Twitter™, Facebook™, etc. and be connected to a video on YouTube™ or another video sharing site. Such a user is interested in seamless integration between the link on the social media site and the playing of the video on the video streaming site. The video streaming site can be a live-streaming video site.

An analytics researcher or "uploader" can be a user who is interested in tracking video performance of one or more videos over time. The performance of the one or more videos can be based on various metrics, including emotional engagement of one or more viewers as they view the one or more videos. The analytics researcher can be interested primarily in the various metrics that are generated based on a given video. The analytics can be based on demographic data, geographic data, and so on. Analytics can also be based on trending search terms, popular search terms, and so on, where the search terms can be identified using web facilities such as Google Trends™.

A quantified self-user can be a user who is interested studying and/or documenting her or his own video watching experiences. The qualified self-user can review her or his mental state data over time, sort a list of viewed videos over a time period, and so on. The qualified self-user can compare their mental state data that is collected while watching a given video with their personal norms. This user persona can also provide feedback. The quantified self-user can track their reactions to one or more videos over time and over videos, where tracking over videos can include tracking favorite videos, categorizing videos that have been viewed, remembering favorite videos, etc.

A music enthusiast can be a user who is a consumer of music who uses a video streaming site such as a music streaming site. For example, this user persona can use music mixes from sites such as YouTube™ as if they were provided by a music streaming site such as Spotify™, Pandora™, Apple Music™, Tidal™, and so on. The music enthusiast persona might be less likely to be sitting in front of a screen, since their main mode of engagement is sound rather than sight. Facial reactions that can be captured from the listener can be weaker, for example, than those facial reactions captured from a viewer.

The method can include comparing the mental state data that was captured against mental state event temporal signatures. In embodiments, the method includes identifying a mental state event type based on the comparing. The recommending of the second media presentation can be based on the mental state event type. The recommending of the second media presentation can be performed using one or more processors. The first media presentation can include a first socially shared live-stream video. The method can further comprise generating highlights for the first socially shared live-stream video, based on the mental state data that was captured. The first socially shared live-stream video can include an overlay with information on the mental state data that was captured. The overlay can include information on the mental state data collected from the other people. The mental state data that was captured for the first socially shared live-stream video can be analyzed substantially in real time. In some embodiments, the second media presentation includes a second socially shared live-stream video. The method can further comprise a recommendation for changing from the first socially shared live-stream video to the second socially shared live-stream video. The first socially shared live-stream video can be broadcast to a plurality of people. In embodiments, the method further comprises providing an indication to the individual that the second socially shared live-stream video is ready to be joined.

Figure 16:
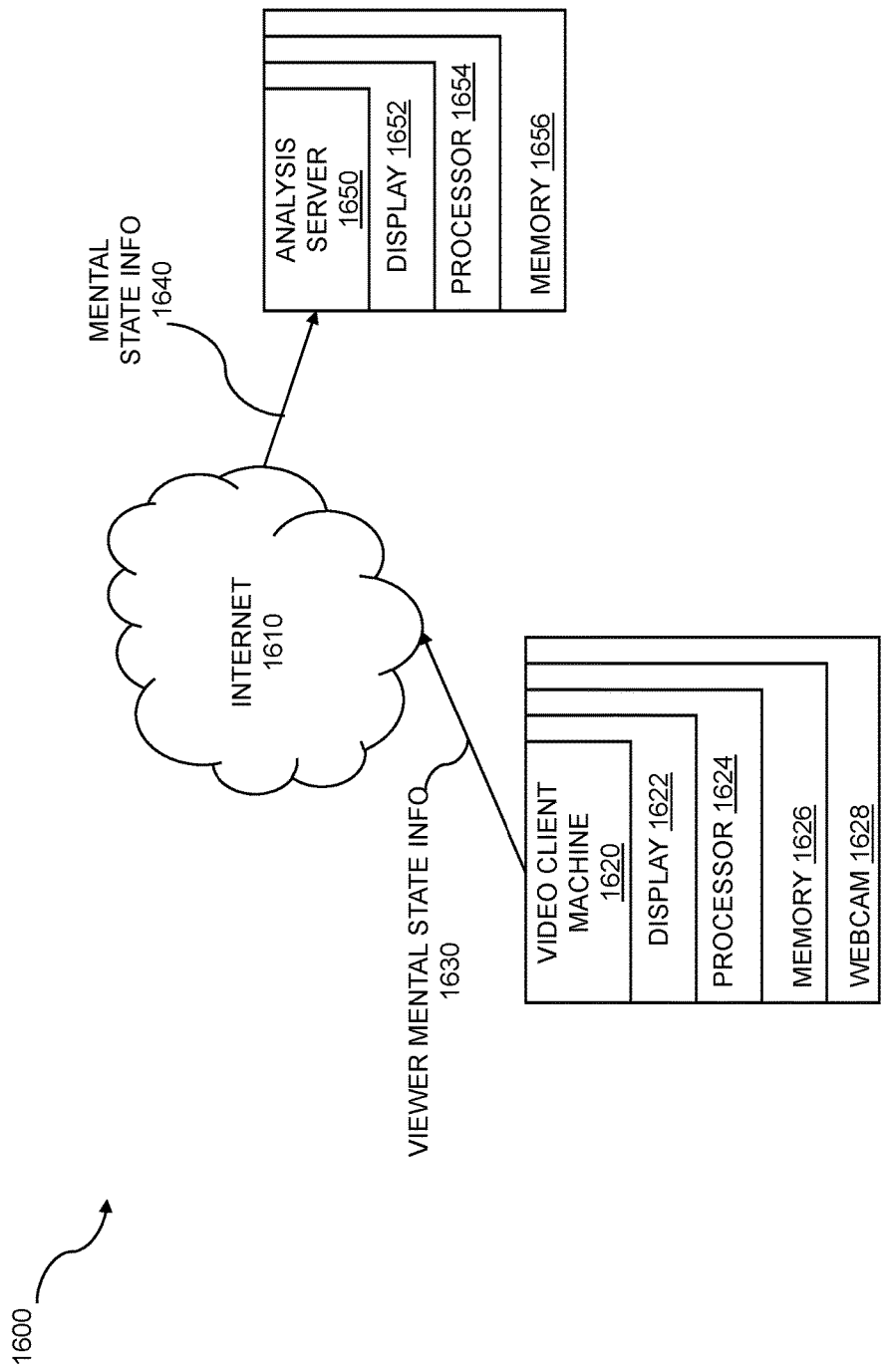
FIG. 16 is a system diagram for analyzing mental state information.

FIG. 16 is a system diagram for analyzing mental state information. The system 1600 can include the Internet 1610, intranet, or another computer network, which can be used for communication between or among the various computers of the system 1600. A video client machine or client computer 1620 can include a memory 1626 which stores instructions, and one or more processors 1624 attached to the memory 1626, wherein the one or more processors 1624 can execute instructions stored in the memory 1626. The memory 1626 can be used for storing instructions, for storing mental state data, for system support, and the like. The client computer 1620 can also have an Internet connection to carry viewer mental state information 1630 and can include a display 1622 that can present various videos to one or more viewers. The client computer 1620 can collect mental state data from one or more viewers as they observe the video or videos. Some embodiments include multiple client computers 1620 that collect mental state data from viewers as they observe a video. The video client computer 1620 can include a camera, such as a webcam 1628, for capturing viewer interaction with a video including, in some embodiments, video of the viewer. The camera 1628 can refer to a webcam, a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that can allow image data captured to be used by the electronic system.

Once the mental state data has been collected, the client computer can upload information to a server or analysis computer 1650, based on the mental state data from the plurality of viewers who observe the video. The client computer 1620 can communicate with the server 1650 over the Internet 1610, intranet, some other computer network, or by any other method suitable for communication between two computers. In some embodiments, the analysis computer 1650 functionality is embodied in the client computer.

The analysis computer 1650 can be connected to the Internet 1610 to enable mental state information 1640 to be received by the analysis computer 1650. Further, the analysis computer 1650 can include a memory 1656 which stores instructions, data, help information and the like, and one or more processors 1654 attached to the memory 1656 wherein the one or more processors 1654 can execute instructions. The memory 1656 can be used for storing instructions, for storing mental state data, for system support, and the like. The analysis computer 1650 can use the Internet 1610, or another computer communication method, to obtain mental state information 1640. The analysis computer 1650 can receive mental state information collected from a plurality of viewers from the client computer or computers 1620, and can aggregate mental state information on the plurality of viewers who observe the video.

The analysis computer 1650 can process mental state data or aggregated mental state data gathered from a viewer or a plurality of viewers to produce mental state information about the viewer or plurality of viewers. In some embodiments, the analysis server 1650 obtains viewer mental state information 1630 from the video client 1620. In this case, the mental state data captured by the video client 1620 was analyzed by the video client 1620 to produce mental state information for uploading. Based on the mental state information produced, the analysis server 1650 can project a value based on the mental state information for one or more videos. The analysis computer 1650 can also associate the aggregated mental state information with the rendering and with the collection of norms for the context being measured.

In some embodiments, the analysis computer 1650 can receive or provide aggregated mental state information based on the mental state data from the plurality of viewers who observe the video and can present aggregated mental state information in a rendering on a display 1652. In some embodiments, the analysis computer is set up for receiving mental state data collected from a plurality of viewers as they observe the video, in a real-time or near real-time embodiment. In at least one embodiment, a single computer incorporates the client, server and analysis functionalities. Viewer mental state data can be collected from the client computer or computers 1620 to form mental state information on the viewer or plurality of viewers viewing a video. The mental state information resulting from the analysis of the mental state date of a viewer or a plurality of viewers can be used to project a video value based on the mental state information. The system 1600 can include computer program product embodied in a non-transitory computer readable medium comprising: code for playing a first media presentation to an individual, code for capturing mental state data for the individual while the first media presentation is played, and code for recommending a second media presentation to the individual based on the mental state data for the individual which was captured. The system 1600 can include capabilities for affect-based recommendation comprising: a memory for storing instructions, one or more processors attached to the memory wherein the one or more processors are configured to play a first media presentation to an individual, capture mental state data for the individual while the first media presentation is played, and recommend a second media presentation to the individual based on the mental state data for the individual which was captured. The system 1600 can include computer program product embodied in a non-transitory computer readable medium comprising: code for selecting a video; code for embedding the video within a web-enabled interface wherein the web-enabled interface activates collecting of mental state data; and code for distributing the web-enabled interface. The system 1600 can include capabilities for rendering video comprising: a memory for storing instructions; one or more processors attached to the memory wherein the one or more processors are configured to: select a video; embed the video within a web-enabled interface wherein the web-enabled interface activates collecting of mental state data; and distribute the web-enabled interface.

The above methods may be executed on one or more processors on one or more computer systems. Embodiments may include various forms of distributed computing, client/server computing, and cloud based computing. Further, it will be understood that for the flow diagrams in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flow diagram illustrations depict methods, apparatus, systems, and computer program products. Each element of the block diagrams and flow diagram illustrations, as well as each respective combination of elements in the block diagrams and flow diagram illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which may be generally referred to herein as a "circuit," "module," or "system."

A programmable apparatus which executes any of the above-mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for affect based recommendations comprising:
   playing a first media presentation to an individual on a video client;
   capturing mental state data for the individual using the video client, wherein the mental state data includes video facial data from the individual during the first media presentation playing;
   comparing, on an analysis server, the mental state data that was captured for the individual against a plurality of mental state event temporal signatures, wherein the mental state event temporal signatures include a shape of an intensity transition;
   ranking, on the analysis server, the first media presentation relative to another media presentation based on the mental state data which was captured for the individual, wherein the ranking is for the individual;
   correlating, on the analysis server, the mental state data which was captured for the individual to mental state data collected from other people who experienced the first media presentation; and
   recommending, using one or more processors in at least one of the video client and the analysis server, a second media presentation to the individual based on the mental state data which was captured for the individual and the correlating, wherein the recommending the second media presentation to the individual is further based on the comparing of the mental state data to the plurality of mental state event temporal signatures.

2. The method of claim 1 further comprising matching a first event signature, from the plurality of mental state event temporal signatures, against the mental state data that was captured.

3. The method of claim 2 wherein the recommending the second media presentation is further based on the matching of the first event signature.

4. The method of claim 1 wherein the correlating is based on identifying similar likes.

5. The method of claim 1 wherein the correlating is based on identifying and using maximally dissimilar responses during part of the correlating.

6. The method of claim 1 further comprising identifying a mental state event type based on the comparing.

7. The method of claim 6 wherein the recommending of the second media presentation is further based on the mental state event type.

8. The method of claim 1 wherein the first media presentation includes a first socially shared live-stream video.

9. The method of claim 8 further comprising generating highlights for the first socially shared live-stream video, based on the mental state data that was captured.

10. The method of claim 8 wherein the first socially shared live-stream video includes an overlay with information on the mental state data that was captured.

11. The method of claim 8 wherein the mental state data that was captured for the first socially shared live-stream video is analyzed substantially in real time.

12. The method of claim 8 wherein the second media presentation includes a second socially shared live-stream video.

13. The method of claim 12 further comprising a recommendation for changing from the first socially shared live-stream video to the second socially shared live-stream video.

14. The method of claim 12 wherein the first socially shared live-stream video is broadcast to a plurality of people.

15. The method of claim 14 further comprising providing an indication to the individual that the second socially shared live-stream video is ready to be joined.

16. The method of claim 1 further comprising performing unsupervised clustering of features extracted from the mental state data.

17. The method of claim 1 further comprising analyzing the mental state data to produce mental state information.

18. The method of claim 17 wherein the analyzing of the mental state data is further based on a demographic basis.

19. The method of claim 1 wherein the ranking is based on anticipated preferences for the individual.

20. The method of claim 1 wherein the mental state data is captured from multiple people and further comprising aggregating the mental state data from the multiple people.

21. The method of claim 20 further comprising ranking the first media presentation relative to another media presentation based on the mental state data which was aggregated from the multiple people.

22. The method of claim 1 wherein the mental state data further includes physiological data or actigraphy data.

23. The method of claim 22 wherein the physiological data includes one or more of electrodermal activity, heart rate, heart rate variability, skin temperature, and respiration.

24. The method of claim 1 further comprising inferring mental states, based on the mental state data which was collected and analysis of the video facial data.

25. The method of claim 24 wherein the analysis of the video facial data is for at least brow furrows.

26. The method of claim 1 wherein the playing of the first media presentation is done on a mobile device and further comprising recording of facial images with the mobile device as part of the capturing of the mental state data.

27. The method of claim 1 wherein at least part of the mental state data collected from other people is captured while the other people view a third media presentation.

28. The method of claim 1 wherein at least part of the mental state data collected from other people is captured while the other people view the first media presentation.

29. The method of claim 1 further comprising determining a correlation vector for the individual based on the correlating.

30. The method of claim 29 further comprising analyzing a difference between the correlation vector for the individual and a correlation vector for at least one of the other people, wherein the recommending is further based on the difference.

31. The method of claim 1 wherein the plurality of mental state event temporal signatures is based on mental state data collected from the other people.

32. The method of claim 1 wherein the shape of the intensity transition included in the mental state event temporal signatures is an intensity transition from a low intensity to a peak intensity.

33. The method of claim 1 wherein the shape of the intensity transition included in the mental state event temporal signatures is an intensity transition from a peak intensity to a low intensity.

34. The method of claim 33 wherein the mental state event temporal signatures include a plurality of shapes of intensity transitions and the shape of at least one intensity transition included in the mental state event temporal signatures is an intensity transition from a low intensity to a peak intensity.

35. A computer program product stored on a non-transitory computer-readable medium for affect based recommendations, the computer program product comprising code which causes one or more processors to perform operations of:
  playing a first media presentation to an individual on a video client;
  capturing mental state data for the individual on the video client, wherein the mental state data includes video facial data from the individual during the first media presentation playing;
  comparing, on an analysis server, the mental state data that was captured for the individual against a plurality of mental state event temporal signatures, wherein the mental state event temporal signatures include a shape of an intensity transition;
  ranking, on the analysis server, the first media presentation relative to another media presentation based on the mental state data which was captured for the individual, wherein the ranking is for the individual;
  correlating, on the analysis server, the mental state data which was captured for the individual to mental state data collected from other people who experienced the first media presentation; and
  recommending, using at least one of the analysis server and the video client, a second media presentation to the individual based on the mental state data which was captured for the individual and the correlating, wherein the recommending the second media presentation to the individual is further based on the comparing of the mental state data to the plurality of mental state event temporal signatures.

36. A computer system for affect based recommendations comprising:
  a memory for storing instructions;
  one or more processors attached to the memory wherein the one or more processors are configured to:
    play a first media presentation to an individual on a video client;
    capture mental state data for the individual using the video client, wherein the mental state data includes video facial data from the individual during the first media presentation playing;
    compare, on an analysis server, the mental state data that was captured for the individual against a plurality of mental state event temporal signatures wherein the mental state event temporal signatures include a shape of an intensity transition;
    rank, on the analysis server, the first media presentation relative to another media presentation based on the mental state data which was captured for the individual, wherein the ranking is for the individual;
    correlate, on the analysis server, the mental state data which was captured for the individual to mental state data collected from other people who experienced the first media presentation; and
    recommend, using at least one of the video client and the analysis server, a second media presentation to the individual based on the mental state data which was captured for the individual and the correlation, wherein the recommending the second media presentation to the individual is further based on comparing of the mental state data to the plurality of mental state event temporal signatures.

* * * * *